United States Patent
Arenas et al.

(10) Patent No.: US 8,354,280 B2
(45) Date of Patent: Jan. 15, 2013

(54) REUSABLE DETECTION SURFACES AND METHODS OF USING SAME

(75) Inventors: Jaime E. Arenas, Lexington, MA (US); Hyun-Goo Choi, Arlington, MA (US); William Matthew Dickerson, Dorchester, MA (US); Sarah Beth Hembree, San Francisco, CA (US); Lara Louise Madison, Bridgewater, MA (US); Brett P. Masters, Belmont, CA (US); Michael F. Miller, Hollis, NH (US); Wayne U. Wang, Cambridge, MA (US)

(73) Assignee: BioScale, Inc., Lexington, MA (US)

( * ) Notice: Subject to any disclaimer, the term of this patent is extended or adjusted under 35 U.S.C. 154(b) by 916 days.

(21) Appl. No.: 12/205,595

(22) Filed: Sep. 5, 2008

(65) Prior Publication Data
US 2009/0068759 A1     Mar. 12, 2009

Related U.S. Application Data

(60) Provisional application No. 60/970,372, filed on Sep. 6, 2007, provisional application No. 61/073,243, filed on Jun. 17, 2008.

(51) Int. Cl.
    *G01N 33/551*     (2006.01)
(52) U.S. Cl. ....... 436/524; 435/286.5; 435/7.1; 435/7.5; 435/7.94; 436/518; 436/526; 436/532; 436/501
(58) Field of Classification Search .................. 435/7.1, 435/7.5, 286.5; 436/501, 526, 518, 524, 436/532
See application file for complete search history.

(56) References Cited

U.S. PATENT DOCUMENTS

| | | | |
|---|---|---|---|
| 4,098,876 A | 7/1978 | Piasio et al. | 424/1 |
| 4,551,435 A | 11/1985 | Liberti et al. | 436/541 |
| 4,596,697 A | 6/1986 | Ballato | 422/98 |
| 4,752,855 A | 6/1988 | Fedter | 361/286 |
| 4,795,698 A | 1/1989 | Owen et al. | 435/4 |
| 4,896,098 A | 1/1990 | Haritonidis et al. | 324/663 |
| 4,920,450 A | 4/1990 | Masiulis | 361/282 |
| 4,925,788 A | 5/1990 | Liberti | 435/7 |
| 4,997,278 A | 3/1991 | Finlan et al. | 356/128 |
| 5,023,053 A | 6/1991 | Finlan | 422/82.05 |
| 5,025,346 A | 6/1991 | Tang et al. | 361/283.1 |
| 5,035,863 A | 7/1991 | Finlan et al. | 422/82.05 |
| 5,047,213 A | 9/1991 | Finlan et al. | 422/82.11 |
| 5,055,265 A | 10/1991 | Finlan | 422/82.05 |

(Continued)

FOREIGN PATENT DOCUMENTS
EP     1752663     2/2007

(Continued)

OTHER PUBLICATIONS

R. M. White, "Direct Piezoelectric Coupling to Surface Elastic Waves," Applied Physics Letters, vol. 7 (Dec. 15, 1965), pp. 314-316.

(Continued)

*Primary Examiner* — Melanie J Yu
*Assistant Examiner* — Erik B Crawford
(74) *Attorney, Agent, or Firm* — Sunstein Kann Murphy & Timbers LLP

(57) ABSTRACT

The technology provided herein generally relates to reusable detection surfaces and methods for reusing a detection surface after using the detection surface in an assay for an analyte.

14 Claims, 10 Drawing Sheets

U.S. PATENT DOCUMENTS

| | | | |
|---|---|---|---|
| 5,064,619 A | 11/1991 | Finlan | 422/82.05 |
| 5,079,600 A | 1/1992 | Schnur et al. | 257/750 |
| 5,108,933 A | 4/1992 | Liberti et al. | 436/501 |
| 5,164,589 A | 11/1992 | Sjödin | 250/227.24 |
| 5,186,827 A | 2/1993 | Liberti et al. | 210/222 |
| 5,189,914 A | 3/1993 | White et al. | 73/599 |
| 5,199,298 A | 4/1993 | Ng et al. | 73/54.01 |
| 5,200,084 A | 4/1993 | Liberti et al. | 210/695 |
| 5,252,743 A | 10/1993 | Barrett et al. | 548/303.7 |
| 5,304,465 A | 4/1994 | Garland et al. | 435/4 |
| 5,306,644 A | 4/1994 | Myerholtz et al. | 436/149 |
| 5,313,264 A | 5/1994 | Ivarsson et al. | 356/73 |
| 5,376,252 A | 12/1994 | Ekström et al. | 204/299 |
| 5,411,709 A | 5/1995 | Furuki et al. | 422/91 |
| 5,436,161 A | 7/1995 | Bergström et al. | 435/291 |
| 5,442,448 A | 8/1995 | Knoll | 356/445 |
| 5,443,890 A | 8/1995 | LÖfashman | 428/167 |
| 5,445,971 A | 8/1995 | Rohr | 436/526 |
| 5,451,683 A | 9/1995 | Barrett et al. | 548/302.7 |
| 5,454,904 A | 10/1995 | Ghezzo et al. | 216/13 |
| 5,455,178 A | 10/1995 | Fattinger | 436/164 |
| 5,479,260 A | 12/1995 | Fattinger | 356/361 |
| 5,482,867 A | 1/1996 | Barrett et al. | 436/518 |
| 5,490,034 A | 2/1996 | Zavracky et al. | 361/283.4 |
| 5,492,840 A | 2/1996 | Malmqvist et al. | 436/518 |
| 5,512,131 A | 4/1996 | Kumar et al. | 438/738 |
| 5,518,887 A | 5/1996 | Parsons et al. | 435/7.1 |
| 5,554,541 A | 9/1996 | Malmqvist et al. | 436/518 |
| 5,593,130 A | 1/1997 | Hansson et al. | 251/61.1 |
| 5,620,850 A | 4/1997 | Bamdad et al. | 530/300 |
| 5,641,640 A | 6/1997 | Hanning | 435/7.92 |
| 5,656,428 A | 8/1997 | McAllister et al. | 435/6 |
| 5,656,504 A | 8/1997 | Johansson et al. | 436/518 |
| 5,660,985 A | 8/1997 | Pieken et al. | 435/6 |
| 5,663,790 A | 9/1997 | Ekström et al. | 356/128 |
| 5,705,402 A | 1/1998 | Leland et al. | 436/526 |
| 5,716,854 A | 2/1998 | Lof.ang.s et al. | 436/518 |
| 5,719,324 A | 2/1998 | Thundat et al. | 73/24.01 |
| 5,744,367 A | 4/1998 | Talley et al. | 436/172 |
| 5,753,518 A | 5/1998 | Karlsson | 436/517 |
| 5,763,191 A | 6/1998 | Knoll et al. | 435/7.1 |
| 5,827,669 A | 10/1998 | Nakayama et al. | 435/7.51 |
| 5,836,203 A | 11/1998 | Martin et al. | 73/579 |
| 5,851,840 A | 12/1998 | Sluka et al. | 436/525 |
| 5,885,527 A | 3/1999 | Buechler | 422/58 |
| 5,900,160 A | 5/1999 | Whitesides et al. | 216/41 |
| 5,912,181 A | 6/1999 | Petcavich | 436/151 |
| 5,922,594 A | 7/1999 | Löfas | 435/291 |
| 5,932,296 A | 8/1999 | Sluka et al. | 427/491 |
| 5,947,124 A | 9/1999 | Buechler et al. | 128/898 |
| 5,955,729 A | 9/1999 | Nelson et al. | 250/282 |
| 5,965,456 A | 10/1999 | Malmqvist et al. | 436/514 |
| 5,972,612 A | 10/1999 | Malmqvist et al. | 435/6 |
| 6,006,589 A | 12/1999 | Rodahl et al. | 73/54.41 |
| 6,008,893 A | 12/1999 | Roos et al. | 356/246 |
| 6,019,944 A | 2/2000 | Buechler | 422/58 |
| 6,033,852 A | 3/2000 | Andle et al. | 435/6 |
| 6,046,585 A | 4/2000 | Simmonds | 324/239 |
| 6,106,779 A | 8/2000 | Buechler et al. | 422/55 |
| 6,123,819 A | 9/2000 | Peeters | 204/403 |
| 6,127,183 A | 10/2000 | Ivarsson et al. | 436/34 |
| 6,143,513 A | 11/2000 | Löfas | 435/24 |
| 6,143,574 A | 11/2000 | Karlsson et al. | 436/517 |
| 6,143,576 A | 11/2000 | Buechler | 436/518 |
| 6,156,270 A | 12/2000 | Buechler | 422/58 |
| 6,194,223 B1 | 2/2001 | Herrmann et al. | 436/518 |
| 6,197,515 B1 | 3/2001 | Bamdad et al. | 435/6 |
| 6,200,814 B1 | 3/2001 | Malmqvist et al. | 436/52 |
| 6,207,381 B1 | 3/2001 | Larsson et al. | 435/6 |
| 6,221,674 B1 | 4/2001 | Sluka et al. | 436/166 |
| 6,222,619 B1 | 4/2001 | Herron et al. | 356/39 |
| 6,271,040 B1 | 8/2001 | Buechler | 436/170 |
| 6,287,758 B1 | 9/2001 | Okun et al. | 435/4 |
| 6,289,286 B1 | 9/2001 | Andersson et al. | 702/19 |
| 6,295,861 B1 | 10/2001 | Tom et al. | 73/24.06 |
| 6,297,060 B1 | 10/2001 | Nowakowski et al. | 436/518 |
| 6,302,919 B1 | 10/2001 | Chambers et al. | |
| 6,306,614 B1 | 10/2001 | Romaschin et al. | 435/7.2 |
| 6,322,979 B1 | 11/2001 | Bamdad et al. | 435/6 |
| 6,326,563 B1 | 12/2001 | Takeuchi et al. | 177/210 FP |
| 6,329,209 B1 | 12/2001 | Wagner et al. | 436/518 |
| 6,348,318 B1 | 2/2002 | Valkirs | 435/7.1 |
| 6,365,418 B1 | 4/2002 | Wagner et al. | 436/518 |
| 6,368,877 B1 | 4/2002 | Zhang et al. | 436/527 |
| 6,437,563 B1 | 8/2002 | Simmonds et al. | 324/239 |
| 6,454,924 B2 | 9/2002 | Jedrzejewski et al. | 204/601 |
| 6,455,980 B1 | 9/2002 | Bernstein | 310/324 |
| 6,457,361 B1 | 10/2002 | Takeuchi et al. | 73/580 |
| 6,472,148 B1 | 10/2002 | Bamdad et al. | 435/6 |
| 6,475,808 B1 | 11/2002 | Wagner et al. | 436/518 |
| 6,485,982 B1 | 11/2002 | Charlton | 436/514 |
| 6,493,097 B1 | 12/2002 | Ivarsson | 356/630 |
| 6,503,760 B2 | 1/2003 | Malmqvist et al. | 436/518 |
| 6,506,620 B1 | 1/2003 | Scharf et al. | 438/52 |
| 6,509,059 B2 | 1/2003 | Yang et al. | 427/230 |
| 6,511,915 B2 | 1/2003 | Mlcak | 438/695 |
| 6,518,168 B1 | 2/2003 | Clem et al. | 438/623 |
| 6,518,747 B2 | 2/2003 | Sager et al. | 324/204 |
| 6,544,674 B2 | 4/2003 | Tuller et al. | 428/698 |
| 6,586,232 B2 * | 7/2003 | Tom-Moy et al. | 435/285.2 |
| 6,589,727 B1 | 7/2003 | Klenerman et al. | 435/4 |
| 6,589,798 B1 | 7/2003 | Löfas | 436/518 |
| 6,596,545 B1 | 7/2003 | Wagner et al. | 436/518 |
| 6,607,922 B2 | 8/2003 | LaBorde | 436/514 |
| 6,627,404 B1 | 9/2003 | Buechler et al. | 435/7.1 |
| 6,627,959 B1 | 9/2003 | Tuller et al. | 257/367 |
| 6,627,965 B1 | 9/2003 | Tuller et al. | 257/415 |
| 6,630,358 B1 | 10/2003 | Wagner et al. | 436/518 |
| 6,647,764 B1 | 11/2003 | Paul et al. | 73/54.41 |
| 6,669,907 B1 | 12/2003 | Buechler | 422/58 |
| 6,688,158 B2 | 2/2004 | Cunningham et al. | 73/24.06 |
| 6,698,454 B2 | 3/2004 | Sjölander et al. | 137/885 |
| 6,716,620 B2 | 4/2004 | Bashir et al. | 435/287.2 |
| 6,720,710 B1 | 4/2004 | Wenzel et al. | 310/328 |
| 6,767,510 B1 | 7/2004 | Buechler | 422/58 |
| 6,775,003 B2 | 8/2004 | Ivarsson | 356/445 |
| 6,790,775 B2 | 9/2004 | Fartash | 438/667 |
| 6,795,273 B2 | 9/2004 | Minor et al. | 360/126 |
| 6,848,295 B2 | 2/2005 | Auner et al. | 73/24.06 |
| 6,901,278 B1 | 5/2005 | Notelovitz | 600/407 |
| 6,936,424 B1 | 8/2005 | Watkins et al. | 435/7.1 |
| 7,118,922 B1 | 10/2006 | Bhansali et al. | 436/518 |
| 7,410,811 B2 | 8/2008 | Lin et al. | 436/526 |
| 2002/0012929 A1 | 1/2002 | Malmqvist et al. | 435/6 |
| 2002/0028519 A1 | 3/2002 | Yguerabide et al. | 436/518 |
| 2002/0042074 A1 | 4/2002 | Bamdad et al. | 435/6 |
| 2002/0048534 A1 | 4/2002 | Storek et al. | 422/99 |
| 2002/0048821 A1 | 4/2002 | Storek et al. | 436/174 |
| 2002/0070841 A1 | 6/2002 | Doppalapudi et al. | 338/5 |
| 2002/0086436 A1 | 7/2002 | Buechler | 436/164 |
| 2002/0094572 A1 | 7/2002 | Singhvi et al. | 435/395 |
| 2002/0115198 A1 | 8/2002 | Nerenberg et al. | 435/287.2 |
| 2002/0128593 A1 | 9/2002 | Sjolander et al. | 604/22 |
| 2002/0164819 A1 | 11/2002 | Storek et al. | 436/174 |
| 2002/0182717 A1 | 12/2002 | Karlsson | 435/287.2 |
| 2003/0010745 A1 | 1/2003 | Field | 216/2 |
| 2003/0012693 A1 | 1/2003 | Otillar et al. | 422/58 |
| 2003/0022388 A1 | 1/2003 | Roos et al. | 436/164 |
| 2003/0035758 A1 | 2/2003 | Buechler et al. | 422/101 |
| 2003/0100762 A1 | 5/2003 | Kaler et al. | 544/296 |
| 2003/0119220 A1 | 6/2003 | Mlcak et al. | 438/52 |
| 2003/0154031 A1 | 8/2003 | Potyrailo et al. | 702/19 |
| 2003/0194710 A1 | 10/2003 | Yang | 435/6 |
| 2004/0002167 A1 | 1/2004 | Andersson et al. | 436/518 |
| 2004/0016297 A1 | 1/2004 | Paul et al. | 73/580 |
| 2004/0023413 A1 | 2/2004 | Opalsky | 436/518 |
| 2004/0038195 A1 | 2/2004 | Nerenberg et al. | 435/4 |
| 2004/0043423 A1 | 3/2004 | Bellew et al. | 435/7.1 |
| 2004/0043615 A1 | 3/2004 | Yamamoto et al. | 438/689 |
| 2004/0058456 A1 | 3/2004 | Safsten et al. | 436/518 |
| 2004/0101990 A1 | 5/2004 | Dunn | 438/48 |
| 2004/0132005 A1 | 7/2004 | Hsu et al. | 435/4 |
| 2004/0161860 A1 | 8/2004 | Richalet-Secordel et al. | 436/518 |
| 2004/0166549 A1 | 8/2004 | Karlsson et al. | 435/7.92 |
| 2004/0166577 A1 | 8/2004 | Storek et al. | 435/287.2 |
| 2004/0241724 A1 | 12/2004 | Karlsson et al. | 435/6 |

| | | | |
|---|---|---|---|
| 2004/0241748 A1* | 12/2004 | Ault-Riche et al. | 435/7.1 |
| 2004/0248213 A1 | 12/2004 | Karlsson et al. | 435/7.2 |
| 2005/0012431 A1 | 1/2005 | Andle | 310/331 D |
| 2005/0014179 A1 | 1/2005 | Karlsson et al. | 435/6 |
| 2005/0019933 A1 | 1/2005 | Andersson et al. | 436/52 |
| 2005/0040907 A1 | 2/2005 | Nebrigic | 332/118 |
| 2005/0057302 A1 | 3/2005 | Andle | 329/370 |
| 2005/0064619 A1 | 3/2005 | Chavan et al. | 438/52 |
| 2005/0074904 A1 | 4/2005 | Chin et al. | 436/526 |
| 2005/0148147 A1 | 7/2005 | Keating et al. | 438/299 |
| 2006/0019330 A1 | 1/2006 | Lakshmi et al. | 435/34 |
| 2007/0224700 A1* | 9/2007 | Masters | 436/501 |
| 2010/0075347 A1* | 3/2010 | Dasaratha et al. | 435/7.33 |

FOREIGN PATENT DOCUMENTS

| | | |
|---|---|---|
| WO | 2004/053105 | 6/2004 |
| WO | 2005/111426 | 11/2005 |
| WO | 2006/119308 | 9/2006 |
| WO | 2007/075619 | 5/2007 |

OTHER PUBLICATIONS

K. Toda, "Lamb-wave delay lines with interdigital electrodes," J. Appl. Phys., vol. 44 (Jan. 1973), pp. 56-62.

M. Lewis, "Surface acoustic wave devices and applications: 6. Oscillators—the next successful surface acoustic wave device?," Ultrasonics, May 1974, pp. 115-123.

J. F. Dias et al., "Frequency/Stress Sensitivity of S.A.W. Resonators," Electronics Letters, vol. 12, No. 22, Oct. 1976, pp. 580-582.

P. Das, "A Pressure Sensing Acoustic Surface Wave Resonator," 1976 Ultrasonics Symposium Proceedings, IEEE, 1976, pp. 306-308.

T. Reeder et al., "Surface-Acoustic-Wave Pressure and Temperature Sensors," Proceedings of the IEEE, vol. 64 (May 1976), pp. 754-756.

S. W. Wenzel, "Applications of Ultrasonic Lamb Waves," dissertation submitted in partial satisfaction of the requirements for the degree of Doctor of Philosophy in Engineering/Electrical Engineering and Computer Sciences, University of California at Davis (1982).

R. M. Langdon, "Resonator sensors—a review," Journal of Physics E: Scientific Instruments, vol. 18, No. 2, 1985, pp. 103-115.

T. Gast, "Sensors with oscillating elements," J. Phys. E: Sci. Instrum., vol. 18, 1985, pp. 783-789.

R. M. White, "Thermoelastic Coupling to Lamb Waves," IEEE Ultrasonics Symposium (1986), pp. 411-415.

D. Hauden, "Miniaturized Bulk and Surface Acoustic Wave Quartz Oscillators Used as Sensors," IEEE Transactions of Ultrasonics, Ferroelectrics, and Frequency Control, vol. UFFC-34, No. 2, Mar. 1987, pp. 253-258.

R. M. White et al., "Plate-Mode Ultrasonic Oscillator Sensors," IEEE Transactions on Ultrasonics, Ferroelectrics, and Frequency Control, vol. 34 (Mar. 1987), pp. 162-171.

S. W. Wenzel et al., "Analytic comparison of the sensitivities of bulk-wave, surface-wave, and flexural plate-wave ultrasonic gravimetric sensors," Appl. Phys. Lett., vol. 54, No. 20, May 15, 1989, pp. 1976-1978.

F. Josse et al., "Analysis of Piezoelectric Bulk-Acoustic-Wave Resonators as Detectors in Viscous Conductive Liquids," IEEE Transactions on Ultrasonics, Ferroelectrics and Frequency Control, vol. 37, No. 5, Sep. 1990, pp. 359-368.

T. Nomura et al., "Measurement of Acoustic Properties of Liquids Using SH-Type Surface Acoustic Waves," Ultrasonics Symposium (1990), p. 307-310, Tokyo, Japan.

W. C. Tang, "Electrostatic Comb Drive for Resonant Sensor and Actuator Applications," Ph.D. Thesis, Electrical Engineering and Computer Sciences, University of California Berkeley, Berkeley, CA, Nov. 1990.

G. M. Whitesides et al., "Wet Chemical Approaches to the Characterization of Organic Surfaces: Self-Assembled Monolayers, Wetting, and the Physical-Organic Chemistry of the Solid-Liquid Interface," Langmuir, vol. 6 (1990), pp. 87-96.

R. L. Baer et al., "Phase Noise Measurements of Flexural Plate Wave Ultrasonic Sensors," 1991 IEEE Ultrasonics Symposium, 1991, pp. 321-326.

J. W. Grate et al., "Flexural Plate Wave Devices for Chemical Analysis," Analytical Chemistry, vol. 63, 1991, pp. 1552-1561.

D. Johannsmann et al., "Visco-elastic properties of thin films probed with a quartz crystal resonator," Makromol. Chem., Macromol. Symp., vol. 46, 1991, pp. 247-251.

K. Martin et al., "Characterization of a Quartz Crystal Microbalance with Simultaneous Mass and Liquid Loading," Analytical Chemical., vol. 63, 1991, pp. 2272-2281.

S. Sjölander et al., "Integrated Fluid Handling System for Biomolecular Interaction Analysis," Anal. chem., vol. 63 (1991), pp. 2338-2345.

B. J. Costello et al., "A Flexural-Plate-Wave Microbial Sensor," IEEE, 0-7803-0456-X/92, pp. 69-72.

Gianchandani et al., "A Bulk Silicon Dissolved Wafer Process for Microelectromechanical Devices," Journal of Microelectromechanical Systems, vol. 1, No. 2, Jun. 1992, pp. 77-85.

J. W. Grate et al., "Frequency-Independent and Frequency-Dependent Polymer Transitions Observed on Flexural Plate Wave Ultrasonic Sensors," Analytical Chemistry, vol. 64, 1992, pp. 413-423.

J. F. Ramalho Ortigao et al., "Antisense Effect of Oligodeoxynucleotides with Inverted Terminal Internucleotidic Linkages: A Minimal Modification Protecting against Nucleolytic Degradation," Antisense Research and Development, vol. 2 (1992), pp. 129-146.

A. Kumar et al., "Features of gold having micrometer to centimeter dimensions can be formed through a combination of stamping with an elastomeric stamp and an alkanethiol 'ink' followed by chemical etching," App. Phys. Letter, vol. 63, No. 14, Oct. 4, 1993, pp. 2002-2004.

T. W. Schneider et al., "Electrochemical Quartz Crystal Microbalance Studies of Adsorption and Desorption of Self-Assembled Monolayers of Alkyl Thiols on Gold," J. Am. Chem. Soc., vol. 115, 1993, pp. 12391-12397.

Giesler et al., "Electrostatic excitation and capacitive detection of flexural plate-waves," Sensors and Actuators A, vol. 36, 1993, pp. 113-119.

R. W. Glaser, "Antigen-Antibody Binding and Mass Transport by Convection and Diffusion to a Surface: A Two-Dimensional Computer Model of Binding and Dissociation Kinetics," Analytical Biochemistry, vol. 213, 1993, pp. 152-161.

J. W. Grate et al., "Acoustic Wave Microsensors—Part I" Analytical Chemistry, vol. 65, No. 21, Nov. 1, 1993, pp. 940A-948A.

J. W. Grate et al., "Acoustic Wave Microsensors—Part II" Analytical Chemistry, vol. 65, No. 22, Nov. 15, 1993, pp. 987A-996A.

J. W. Grate et al., "Smart Sensor System for Trace Organophosphorus and Organosulfur Vapor Detection Employing a Temperature-Controlled Array of Surface Acoustic Wave Sensors, Automated Sample Preconcentration, and Pattern Recognition," Analytical Chemistry, vol. 65, No. 14, Jul. 15, 1993, pp. 1868-1881.

S. Loughin et al., "Electronic structure of aluminum nitride: Theory and experiment," Applied Physics Letters, vol. 63, No. 9, Aug. 30, 1993, pp. 1182-1184.

T. Giesler et al., "Electrostatically excited and capacitively detected flexural plate waves on thin silicon nitride membranes with chemical sensor applications," Sensors and Actuators B, vol. 18-19, 1994, pp. 103-106.

A. Kumar et al., "Pattering Self-Assembled Monolayers: Applications in Material Science," Langmuir, vol. 10, 1994, pp. 1498-1511.

H. Ron et al., "Alkanethiol Monolayers on Preoxidized Gold. Encapsulation of Gold Oxide under an Organic Monolayer," Langmuir, vol. 10, 1994, pp. 4566-4573.

S. Martin et al., "Dynamics and Response of Polymer-Coated Surface Acoustic Wave Devices: Effect of Biscoelastic Properties and Film Resonance," Analytical Chemistry, vol. 66 (1994), pp. 2201-2219.

P. Wagner et al., "Covalent anchoring of proteins onto gold-directed NHS-terminated self-assembled monolayers in aqueous buffers: SFM images of clathrin cages and triskelia," FEBS Letters, vol. 356 (1994), pp. 267-271.

R. A. McGill et al., "Choosing polymer coatings for chemical sensors," Chemtech (Sep. 1994), p. 27-37.

S. Löfas, "Dextran modified self-assembled monolayer surfaces for use in biointeraction analysis with surface plasmon resonance," Pure & Appl. Chem., vol. 67, No. 5, 1995, pp. 829-834.

J. W. Grate et al., "Dewetting Effects on Polymer-Coated Surface Acoustic Wave Vapor Sensors," Analytical Chemistry, vol. 67, No. 21, Nov. 1, 1995, pp. 4015-4019.

M. Rodahl et al., "Quartz crystal microbalance setup for frequency and $Q$-factor measurements in gaseous and liquid environments," Rev. Sci. Instrum, vol. 66 (Jul. 1995) pp. 3924-3930.

C. P. Quinn et al., "Copolymers for improving biocompatibility of biosensors," Biomaterials, vol. 16 (1995), pp. 389-396.

M. Mrksich et al., "Surface Plasmon Resonance Permits in Situ Measurement of Protein Adsorption on Self-Assembled Monolayers of Alkanethiolates on Gold," Langmuir, vol. 11 (1995), pp. 4383-4385.

E. H. Yang et al, "A technique for quantitative determination of the profile of the residual stress along the depth of $p^+$ silicon films," Appl. Phys. Lett, vol. 67 (Aug. 14, 1995), pp. 912-914.

M. Iyer et al., "Accelerated Hybridization of Oligonucleotides to Duplex DNA," The Journal of Biological Chemistry, vol. 270 (Jun. 16, 1995), pp. 14712-14717.

G. M. Kuziemko et al., "Cholera Toxin Binding Affinity and Specificity for Gangliosides Determined by Surface Plasmon Resonance," Biochemistry, vol. 35, 1996, pp. 6375-6384.

M. Mrksich et al., "Using Self-Assembled Monolayers to Understand the Interactions of Man-Made Surfaces with Proteins and Cells," Annu. Rev. Biophys. Biomol. Struct., vol. 25, 1996, pp. 55-78.

K. Nakanishi et al., "A Novel Method of Immobilizing Antibodies on a Quartz Crystal Microbalance Using Plasma-Polymerized Films for Immunosensors," Analytical Chemistry, vol. 68, No. 10, May 15, 1996, pp. 1695-1700.

I. Shalish et al., "Gold metallization for aluminum nitride," Thin Solid Films, vol. 28 (1996), pp. 166-169.

S. Shi-Hui et al., "Bulk acoustic wave sensor for investigation hemorheoloical characteristics of plasma and its coagulation," J. Biochem. Biophys. Methods, vol. 31 (1996), pp. 135-143.

A. Ullman, "Formation and Structure of Self-Assembled Monolayers," Chem. Rev., vol. 96 (1996), pp. 1533-1554.

B. A. Warneke, "Triaxial Monolithic Piezoresistive Accelerometers in Foundry CMOS," Masters Thesis, Electrical Engineering, University of California, Los Angeles, CA (1996).

G. Sigal et al., "A Self-Assembled Monolayer for the Binding and Study of Histidine-Tagged Proteins by Surface Plasmon Resonance," Anal. Chem., vol. 68 (1996), pp. 490-497.

P. M. Richalet-Sécordel et al., "Concentration Measurement of Unpurified Proteins Using Biosensor Technology under Conditions of Partial Mass Transport Limitation," Analytical Biochemistry, vol. 249, 1997, pp. 165-173.

A. F. Collings et al., "Biosensors: recent advances," Rep. Prog. Phys., vol. 60, 1997, pp. 1397-1445.

B. A. Čavić et al., "Acoustic waves and the real-time study of biochemical macromolecules at the liquid/solid interface," Faraday Discuss., vol. 107, 1997, pp. 159-176.

L. Christensen, "Theoretical Analysis of Protein Concentration Determination Using Biosensor Technology under Conditions of Partial Mass Transport Limitation," Analytical Biochemistry, vol. 249, 1997, pp. 153-164.

N. Patel et al., "Immobilization of Protein Molecules onto Homogeneous and Mixed Carboxylate-Terminated Self-Assembled Monolayers," Langmuir, vol. 13, 1997, pp. 6485-6490.

R. R. Seigel et al., "On-Line Detection of Nonspecific Protein Adsorption at Artificial Surfaces," Analytical Chemistry, vol. 69, No. 16, Aug. 15, 1997. pp. 3321-3328.

M. B. Medina et al., "Real-time analysis of antibody binding interactions with immobilized E. coli 0157:H7 cells using the BIAcore," Biotechnology Techniques, vol. 11, No. 3, Mar. 1997, pp. 173-176.

M. Takayasu et al., "Continuous Magnetic Separation of Blood components from Whole Blood," 16th International Conference on Magnet Technology, Florida, USA, 1999.

M. Rodahl et al., "Simultaneous frequency and dissipation factor QCM measurements of biomolecular adsorption and cell adhesion," Faraday Discuss, vol. 107 (1997), pp. 229-246.

X. Wang, "Dielectrophoretic Manipulation of Particles," IEEE Transactions on Industry Applications, vol. 33 (May/Jun. 1997), pp. 660-669.

R. M. White, "Introductory Lecture—Acoustic interactions from Faraday's crispations to MEMS," Faraday Discuss, vol. 107 (1997), pp. 1-13.

D. S. Ballantine, Jr. et al., "Acoustic Wave Sensors—*Theory, Design, and Physico-Chemical Applications*," Academic Press, New York, 1997.

H. Yu et al., "Development of a Magnetic Microplate Chemifluorimmunoassay for Rapid Detection of Bacteria and Toxin in Blood," Analytical Biochemistry, vol. 261, 1998, pp. 1-7.

R. C. Anderson et al., "Genetic Analysis Systems: Improvements and Methods," Solid-State Sensor and Actuator Workshop, Hilton Head Island, South Carolina, Jun. 8-11, 1998, pp. 7-10.

D. G. Myszka et al., "Extending the Range of Rate Constants Available from BIACORE: Interpreting Mass Transport-Influenced Binding Data," Biophysical Journal, vol. 75, Aug. 1998, pp. 583-594.

C. Bisson et al., "A Microanalytical Device for the Assessment of Coagulation Parameters in Whole Blood," Solid-State Sensor and Actuator Workshop, Hilton Head Island, South Carolina, Jun. 8-11, 1998, pp. 1-6.

A. S. Blawas et al., "Protein patterning," Biomaterials, vol. 19, 1998, pp. 595-609.

J. D. Brewster, "Automated filtration capture immunoelectrochemical assay of bacteria," Proceedings of SPIE Reprint, Reprinted from Pathogen Detection and Remediation for Safe Eating, Nov. 5, 1998, Boston, MA.

L. D. Burke et al., "The Electrochemistry of Gold: II The Electrocatalytic Behaviour of the Metal in Aqueous Media," Gold Bulletin, vol. 31, No. 2, 1998, pp. 39-50.

J. M. Bustillo et al., "Surface Micromachining for Microelectromechanical Systems," Proceedings of the IEEE, vol. 86, No. 8, Aug. 1998, pp. 1552-1574.

G. M. Cruise et al., "Characterization of permeability and network structure of interfacially photopolymerized poly(ethylene glycol) diacrylate hydrogels," Biomaterials, vol. 19, 1998, pp. 1287-1294.

J. L. Dohner, "The Contribution of Radiation and Viscous Loss in a Fluid Loaded Flexural Plate Wave Sensor," Journal of Sound and Vibration, vol. 217, No. 1, 1998, pp. 113-126.

D. L. Elbert et al., "Self-assembly and steric stabilization at heterogeneous, biological surfaces using adsorbing block copolymers," Chemistry & Biology, vol. 5, Mar. 13, 1998, pp. 177-183.

J. C. Pyun et al., "Development of a biosensor for *E. coli* based on a flexural plate wave (FPW) transducer," Biosensors & Bioelectronics, vol. 13, 1998, pp. 839-845.

J. M. Van Emon et al., "Bioseparation and bioanalytical techniques in environmental monitoring," Journal of Chromatography B, vol. 715, 1998, pp. 211-228.

I. Ladabaum et al., "Surface Micromachined Capacitive Ultrasonic Transducers," IEEE Transactions on Ultrasonics, Ferroelectrics, and Frequency Control, vol. 45, No. 3, May 1998, pp. 678-690.

H. Ron et al., "Self-Assembled Monolayers on Oxidized Metals. 2. Gold Surface Oxidative Pretreatment, Monolayer Properties, and Depression Formation," Langmuir, vol. 14, 1998, pp. 1116-1121.

N. Yazdi et al., "Micromachined Inertial Sensors," Proceedings of the IEEE, vol. 86, No. 8, Aug. 1998, pp. 1640-1659.

P. Creter et al, "A Systems Approach to Specifying a High Reliability, High Quality Thick Film Passive Component for Hybrid, Multi-Ship Module and Surface Mount Applications," reprint from IMPAS, International Symposium of Microelectronics, (Nov. 4, 1998), San Diego, CA.

H. Chou et al., "Disposable Microdevices for DNA Analysis and Cell Sorting," Proc. Solid-State Sensor and Actuator Workshop, Hilton Head, SC (Jun. 8-11, 1998), pp. 11-14.

S. Storri et al., "Surface modifications for the development of piezoimmunosensors," Biosensors & Bioelectronics, vol. 13, No. 3-4, 1998, pp. 347-357.

A. W. Wang et al., "A Silicon-based Immunoassay for Detection of Breast Cancer Antigens," Sensors and Actuators B, vol. 49 (1998), pp. 13-21.

C. Zhou et al., "Acoustic standing-wave enhancement of a fiber-optic *Salmonella* biosensor," Biosensors & Bioelectronics, vol. 13 (1998), pp. 495-500.

M. J. Feldstein et al., "Array Biosensor: Optical and Fluidics Systems," Journal of Biomedical Microdevices, vol. 1, No. 2, 1999, pp. 139-153.

K. Andersson et al., "Identification and Optimization of Regeneration Conditions for Affinity-Based Biosensor Assays. A Multivariate Cocktail Approach," Analytical Chemistry, vol. 71, No. 13, Jul. 1, 1999, pp. 2475-2481.

R. A. Scott et al., "Highly crosslinked, PEG-containing copolymers for sustained solute delivery," Biomaterials, vol. 20, 1999, pp. 1371-1380.

H. Weetall, "Chemical sensors and biosensors, update, what, where, when and how," Biosensors & Bioelectronics, vol. 14, 1999, pp. 237-242.

S. E. Cowan et al., "Ultrasonic Flexural-Plate-Wave Sensor for Detecting the Concentration of Settling E. coli W3110 Cells," Analytical Chemistry, vol. 71, No. 16, Aug. 15, 1999, pp. 3622-3625.

R. Ekins et al, "Microarrays: their origins and applications," TIBTECH, vol. 17, Jun. 1999, pp. 217-218.

C. Yan et al., "Formation of Alkanethiolate Self-Assembled Monolayers on Oxidized Gold Surfaces," Langmuir, vol. 15, 1999, pp. 2414-2419.

A. Halperin, "Polymer Brushes that Resist Adsorption of Model Proteins: Design Parameters," Langmuir, vol. 15, 1999, pp. 2525-2533.

B. Heymann et al, "Elastic properties of poly(ethylene-glycol) studied by molecular dynamics stretching simulations," Chemical Physics Letters, vol. 307, 1999, pp. 425-432.

G. J. Kluth et al., "Direct observation of sulfur dimmers in alkanethiol self-assembled monolayers on Au(111)," Physical Review B, Rapid Communications, vol. 59, No. 16, Apr. 15, 1999, pp. R10 449-R10 452.

R. Lucklum et al., "Role of Mass Accumulation and Viscoelastic Film Properties for the Response of Acoustic-WaveBased Chemical Sensors," Analytical Chemistry, vol. 71, No. 13, Jul. 1, 1999, pp. 2488-2496.

S. W. Metzger et al., "Development and characterization of surface chemistries for microfabricated biosensors," J. Vac. Sci. Technol. A, vol. 17, No. 5, Sep./Oct. 1999, pp. 2623-2628.

D. Ivnitski et al., "Biosensors for detection of pathogenic bacteria," Biosensors & Bioelectronics, vol. 14, 1999, pp. 599-624.

S. Kim et al., "The Fabrication of Thin-Film Bulk Acoustic Wave Resonators Employing a ZNO/Si Composite Diaphragm Structure Using Porous Silicon Layer Etching," IEEE Electron Device Letters, vol. 20 (Mar. 1999), p. 113-115.

B. D. Spangler et al., "Capture agents for a quartz crystal microbalance-continuous flow biosensor: functionalized self-assembled monolayers on gold," Analytica Chimica Acta, vol. 399 (1999), pp. 51-62.

M. V. Voinova et al., "Viscoelastic Acoustic Response of Layered Polymer Films at Fluid-Solid Interfaces: Continuum Mechanics Approach," Physica Scripta, vol. 59 (1999), pp. 391-396.

J. Yang et al., "Cell Separation on Microfabricated Electrodes Using Dielectrophoretic/Gravitational Field-Flow Fractionation," Anal. Chem., vol. 71 (1999), pp. 911-918.

G. L. Kenausis et al., "Poly(L-lysine)-g-Poly(ethylene glycol) Layers on Metal Oxide Surfaces: Attachment Mechanism and Effects of Polymer Architecture on Resistance to Protein Adsorption," J. Phys. Chem. B, vol. 104, 2000, pp. 3298-3309.

G. Bitko et al., "Improving the MEMS Pressure Sensor," Sensors Magazine, Jul. 2000.

C. A. Rowe-Taitt et al., "Simultaneous detection of six biohazardous agents using a planar waveguide array biosensor," Biosensors & Bioelectronics, vol. 15, 2000, pp. 579-589.

C. A. Rowe-Taitt et al., "Array biosensor for detection of biohazards," Biosensors & Bioelectronics, vol. 14, 2000, pp. 785-794.

R. Maboudian et al., "Self-assembled monolayers as anti-stiction coatings for MEMS: characteristics and recent developments," Sensors and Actuators, vol. 82, 2000, pp. 219-223.

R. L. Edelstein et al., "The BARC biosensor applied to the detection of biological warfare agents," Biosensors & Bioelectronics, vol. 14, 2000, pp. 805-813.

T. Viitala et al., "Protein Immobilization to a Partially Cross-Linked Organic Monolayer," Langmuir, vol. 16, 2000, pp. 4953-4961.

Z. J. Davis et al., "Fabrication and characterization of nanoresonating devices for mass detection," J. Vac. Sci. Technol. B, vol. 18, No. 2, Mar./Apr. 2000, pp. 612-616.

N. Einerson, "Poly(ethylene glycol) and its Role in Surface Modification of Biomaterials," BME/Pharmacy 601, Apr. 2000.

A. Janshoff et al., "Piezoelectric Mass-Sensing Devices as Biosensors—An Alternative to Optical Biosensors?," Angew. Chem. Int. Ed., vol. 39, 2000, pp. 4004-4032.

J. T. Woodward et al., "Effect of an Oxidized Gold Substrate on Alkanethiol Self-Assembly," Langmuir, vol. 16, 2000, pp. 5347-5353.

N. Nguyen et al., "Acoustic Streaming in Micromachined Flexural Plate Wave Devices: Numerical Simulation and Experimental Verification," IEEE Transactions on Ultrasonics, Ferroelectrics, and Frequency Control, vol. 47, No. 6, Nov. 2000, pp. 1463-1471.

J. Choi et al., "A new magnetic bead-based, filterless bio-separator with planar electromagnet surfaces for integrated bio-detection systems," Sensors and Actuators B, vol. 68, 2000, pp. 34-39.

S. T. Pathirana et al, "Rapid and sensitive biosensor for Salmonella," Biosensors and Bioelectronics, vol. 15 (2000), pp. 135-141.

Boston MicroSystems—Fluid Sensors, fluid sensors tab, at "http://www.bostonmicrosytems.com/fluidsensors.shtml" (last visited May 25, 2005), pp. 1-3.

K. Rogers, "Principles of Affinity-Based Biosensors," Molecular Biotechnology, vol. 14 (2000), pp. 109-129.

S. Quake et al., "From Micro-to Nanofabrication with Soft Materials," Science, vol. 290 (Nov. 24, 2000), pp. 1536-1540.

F. N. Dulsev et al., "'Hearing' Bond Breakage. Measurement of Bond Rupture Forces Using a Quartz Crystal Microbalance," Langmuir, vol. 16 (2000), pp. 5036-5040.

T. P. Vinkinge et al., "Comparison of surface plasmon resonance and quartz crystal microbalance in the study of whole blood and plasma coagulation," Biosensors & Bioelectronics, vol. 15 (2000), pp. 605-613.

M. S. Weinberg et al., "Modeling Flexural Plate Wave Devices," Journal of Microelectromechanical Systems, vol. 9 (Sep. 2000), pp. 370-379.

K. F. Jensen, "Microreaction engineering—is small better?," Chemical Engineering Science, vol. 56, 2001, pp. 293-303.

N. D. Masters et al., "Side-by-Side Comparison of Passive MEMS Strain Test Structures under Residual Compression," Mechanical Properties of Structural Films, Sep. 15, 2001, pp. 1-33.

M. Abrantes et al., "Adaptation of a Surface Plasmon Resonance Biosensor with Microfluidics for Use with Small Sample volumes and Long Contact Times," Analytical Chemistry, vol. 73, No. 13, Jul. 1, 2001, pp. 2828-2835.

M. Johnson, "High Sensitivity Magnetic Sensors for Biotechnology," DARPA Workshop on Bio-Magnetic Interfacing Concepts, Arlington, VA, Dec. 12, 2001.

L. Whitman et al., "A Micromagnetic Gene Chip: Magnetic Labeling and GMR Detection of DNA," BioMagnetICs Workshop, Dec. 12, 2001.

D. P. Chandler et al., "Automated immunomagnetic separation and microarray detection of E. Coli 0157:H7 from poultry carcass rinse," International Journal of Food Microbiology, vol. 70, 2001, pp. 143-154.

J. Choi et al., "Development and Characterization of Microfluidic Devices and Systems for Magnetic Bead-Based Biochemical Detection," Biomedical Microdevices, vol. 3, No. 3, 2001, pp. 191-200.

A. N. Cleland et al., "Single-crystal aluminum nitride nanomechanical resonators," Applied Physics Letters, vol. 79, No. 13, Sep. 24, 2001, pp. 2070-2072.

M. A. Cooper et al., "Direct and sensitive detection of a human virus by rupture event scanning," Nature Biotechnology, vol. 19, Sep. 2001, pp. 833-837.

B. Cunningham et al., "Design, fabrication and vapor characterization of a microfabricated flexural plate resonator sensor and application to integrated sensor arrays," Sensors and Actuators B, vol. 73, 2001, pp. 112-123.

J. M. Dodson et al., "Fluidics Cube for Biosensor Miniaturization," Analytical Chemistry, vol. 73, No. 15, Aug. 1, 2001, pp. 3776-3780.

A. H. Forster et al., "A laminated, flex structure for electronic transport and hybridization of DNA," Biosensors & Bioelectronics, vol. 16, 2001, pp. 187-194.

Y. S. Fung et al., "Self-Assembled Monolayers as the Coating in a Quartz Piezoelectric Crystal Immunosensor to Detect Salmonella in Aqueous Solution," Analytical Chemistry, vol. 73, No. 21, Nov. 1, 2001, pp. 5302-5309.

P. Galambos et al., "Precision Alignment Packaging for Microsystems with Multiple Fluid Connections," Proceeding of 2001 ASME: International Mechanical Engineering Conference and Exposition, Nov. 11-16, 2001, New York, NY, pp. 1-8.

G. P. Hatch et al., "Magnetic design considerations for devices and particles used for biological high-gradient magnetic separation (HGMS) systems," Journal of Magnetism and Magnetic Materials, vol. 225, 2001 pp. 262-276.

N. Huang et al., "Poly(L-lysine)-g-poly(ethylene glycol) Layers on Metal Oxide Surfaces: Surface-Analytical Characterization and Resistance to Serum and Fibrinogen Adsorption," Langmuir, vol. 17, 2001, pp. 489-498.

P. B. Luppa et al., "Immunosensors-principles and applications to clinical chemistry," Clinica Chimica Acta, vol. 314, 2001, pp. 1-26.

M. Ishihara et al., "Synthesis and Surface Acoustic Wave Property of Aluminum Nitride Thin Films Fabricated on Silicon and Diamond Substrates Using the Sputtering Methods," Jpn. J. Appl. Phys., vol. 40, 2001, pp. 5065-5068.

M. K. Jain et al., "Measurement of Temperature and Liquid Viscosity Using Wireless Magneto-Acoustic/Magneto-Optical Sensors," IEEE Transactions on Magnetics, vol. 37, No. 4, Jul. 2001 pp. 2767-2769.

K. Kao et al., "Synthesis of C-Axis-Oriented Aluminum Nitride Films by Reactive RF Magnetron Sputtering for Surface Acoustic Wave," Jpn. J. Appl. Phys., vol. 40, 2001, pp. 4969-4973.

K. E. Sapsford et al., "Kinetics of Antigen Binding to Arrays of Antibodies in Different Sized Spots," Analytical Chemistry, vol. 73, No. 22, Nov. 15, 2001, pp. 5518-5524.

V. Kaajakari et al., "A Frequency Addressable Ultrasonic Microfluidic Actuator Array," Transducers '01, Eurosensors XV, The 11th International Conference on Solid-State Sensors and Actuators, Munich, Germany, Jun. 10-14, 2001.

S. Perez-Amodio et al., "Effects on the Ionic Environment, Charge, and Particle Surface Chemistry for Enhancing a Latex Homogeneous Immunoassay of C-Reactive Protein," Analytical Chemistry, vol. 73, No. 14, Jul. 15, 2001, pp. 3417-3425.

V. Linder et al., "Surface Biopassivation of Replicated Poly(dimethylsiloxane) Microfluidic Channels and Applications to Heterogeneous Immunoreaction with On-Chip Fluorescence Detection," Analytical Chemistry, vol. 73, No. 17, Sep. 1, 2001, pp. 4181-4189.

F. Höök et al., Characterization of PNA and DNA Immobilization and Subsequent Hybridization with DNA Using Acoustic-Shear-Wave Attenuation Measurements, Langmuir, vol. 17 (2001), pp. 8305-8312.

J. Halámek et al., "Investigation of highly sensitive piezoelectric immunosensors for 2,4-dichlorophenoxyacetic acid," Biosensors & Bioelectronics, vol. 16 (2001), pp. 253-260.

E. O. Saphire et al., "Listening for viral infection," Nature Biotechnology, Vo. 19 (Sep. 2001), p. 283-284.

S. Solé, "New materials for electrochemical sensing III. Beads," Trends in Analytical chemistry, vol. 20 (2001), pp. 102-110.

B. D. Spangler et al., "Comparison of the Speeta® surface plasmon resonance sensor and a quartz crystal microbalance for detection of *Escherichia coli* heat-labile enterotoxin," Analytica Chimica Acta, vol. 444 (2001), pp. 149-161.

K. M. Lakin, "Thin Film Resonators and High Frequency Filters," TFR Technologies, Inc., (Jun. 1, 2001), pp. 1-18.

M. Tsai et al., "Preconditioning gold Substrates Influences Organothiol Self-assembled Monolayer (SAM) Formation," Journal of Colloid and Interface Science, vol. 238 (2001), pp. 259-266.

J. Voldman, "A microfabricated dielectrophoretic trapping array for cell-based biological assays," Ph.D. Thesis, Department of Electrical Engineering and Computer Science, M.I.T., Cambridge, MA, Jun. 2001.

B. Zhu et al., "Chain-length dependence of the protein and cell resistance of oligo(ethylene glycol)-terminated self-assembled monolayers on gold," Department of Chemical Engineering, University of Illinois at Urbana-Champaign, Urbana, IL/Department of Veterinary Biosciences, University of Illinois at urbana-Champaign, Urbana, IL (accepted Mar. 10, 2001), John Wiley & Sons, Inc., 2001, pp. 406-416.

L. A. Ruiz-Taylor, "Monolayers of derivatized poly(L-lysine)-grafted poly(ethylene glycol) on metal oxides as a class of biomolecular interfaces," PNAS, vol. 98 (Jan. 30, 2001), pp. 852-857.

P. Irwin et al., "Immuno-Magnetic Bead Mass Transport and Capture Efficiency at Low Target Cell Densities in Phosphate-Buffered Saline," Journal of Rapid Methods and Automation in Microbiology, vol. 10, 2002, pp. 129-147.

S. P. Lal et al., "Antibody arrays: an embryonic but rapidly growing technology," Drug Discovery Today, vol. 7, No. 18 (Suppl.), 2002, pp. S143-S149.

J. P. Black et al., " Microsphere Capture and Perfusion in Microchannels Using Flexural Plate Wave Structures," 2002 IEEE Ultrasonics Symposium, 2002, pp. 475-479.

N. K. Chaki et al., "Self-assembled monolayers as a tunable platform for biosensor applications," Biosensors & Bioelectronics, vol. 17, 2002, pp. 1-12.

P. S. Doyle et al., "Self-Assembled Magnetic Matrices for DNA Separation Chips," Science, vol. 295, Mar. 22, 2002, p. 2237.

J. W. McClaine et al., "Characterizing the Adhesion of Motile and Nonmotile *Escherichia coli* to a Glass Surface Using a Parallel-Plate Flow Chamber," Biotechnology and Bioengineering, vol. 78, No. 2, Apr. 20, 2002, pp. 179-189.

O. Hofmann et al., "Three-Dimensional Microfluidic Confinement for Efficient Sample Delivery to Biosensor Surfaces. Application to Immunoassays on Planar Optical Waveguides," Analytical Chemistry, vol. 74, No. 20, Oct. 15, 2002, pp. 5243-5250.

T. Nishihara et al., "High Performance and Miniature Thin Film Bulk Acoustic Wave filters for 5 GHz," 2002 IEEE Ultrasonics Symposium, 2002.

S. Tokumitsu et al., "Grafting of Alkanethiol-Terminated Poly(ethylene glycol) on Gold," Langmuir, vol. 18, 2002, pp. 8862-8870.

F. S. Ligler et al., "Integrating Waveguide Biosensor," Analytical Chemistry, vol. 74, No. 3, Feb. 1, 2002, pp. 713-719.

C. R Tamanaha et al., "Hybrid macro-micro fluidics system for a chip-based biosensor," Journal of Micromechanics and Microengineering, vol. 12, 2002, pp. N7-N17.

F. Engelmark, "AIN and High-k Thin Films for IC and Electroacoustic Applications," Comprehensive Summaries of Uppsala Dissertations from the Faculty of Science and Technology, vol. 757, ACTA Universitatis Upsaliensis, Uppsala, 2002.

M. V. Voinova et al., "'Missing mass' effect in biosensor's QCM applications," Biosensors & Bioelectronics, vol. 17 (2002), pp. 835-841.

R. Hall, "Biosensor technologies for detecting microbiological foodborne hazards," Microbes and Infection, vol. 4 (2002), pp. 425-432.

Y. Loo et al., "Soft, conformable electrical contacts for organic semi-conductors: High-resolution plastic circuits by lamination," PNAS, vol. 99 (Aug. 6, 2002), pp. 10252-10256.

J. Rossier et al., "Polymer microfluidic chips for electrochemical and biochemical analyses," Electrophoresis, vol. 23 (2002), pp. 858-867.

S. Sharma et al., "Controlling Nonspecific Protein Interactions in Silicon Biomicrosystems with Nanostructured Poly(ethlylene glycol) Films," Langmuir, vol. 18 (2002), pp. 8728-8731.

A. D. Stroock et al., "Chaotic Mixer for Microchannels," Science, vol. 295 (Jan. 25, 2002), pp. 647-651.

F. Mandy et al., "T-Cell Subset Counting and the Fight Against AIDS: Reflections Over a 20-Year Struggle," Cytometry (Clinical Cytometry), vol. 50 (2002), pp. 39-45.

D. Zhang et al., "Synthesis and Single Molecule Force Spectroscopy of Graft Copolymers of Poly (2-hydroxyethyl methacrylate-g-ethylene glycol)," Department of Materials Science and Engineering, Massachusetts Institute of Technology, Cambridge, MA, Jul. 2003, pp. 1-47.

G.W. Ritter, "Using Adhesives Effectively in Medical Devices," available at "http://www.devicelink.com/grabber.php3?URL=http://www.devicelink.com/mddi/archive/..." downloaded Aug. 13, 2003, 7 pages.

L. Ceriotti, "Microfluidic systems for point-of-care testing," Sensors, Actuators and Microsystems Laboratory Institute of Microtechnology, University of Neuchâtel, Neuchâtel, Switzerland, May 21, 2003.

M. Cooper, "Biosensing using rupture event scanning (REVS)™," Measurement Science and Technology, vol. 14, 2003, pp. 1888-1893.

S. D. Richardson, "Water Analysis: Emerging Contaminants and Current Issues," Analytical Chemistry, vol. 75, No. 12, Jun. 15, 2003, pp. 2831-2857.

R. Grace, "Commercialization Issues of MEMS/MST/Micromachines An Updated Industry Report Card On The Barriers to Commercialization," http://www.rgrace.com/Papers/commercial.html, downloaded Jan. 16, 2003.

J. W. Grate, "A Sorptive Behavior of Monolayer-Protected Gold Nanoparticle Films Containing Alkanethiols and Alkanedithiols," Analytical Chemistry, vol. 75, No. 23, Dec. 1, 2003, p. 6759.

D. Sparks et al., "Measurement of density and chemical concentration using a microfluidic chip," Lab Chip, vol. 3, 2003, pp. 19-21.

J. Lahann et al., "Reactive Polymer Coatings: A First Step toward Surface Engineering of Microfluidic Devices," Analytical Chemistry, vol. 75, No. 9, May 1, 2003, pp. 2117-2122.

G. Kim et al., "Impedance characterization of a piezoelectric immunosensor Part I: Antibody coating and buffer solution," Biosensors and Bioelectronics, vol. 18, 2003, pp. 83-89.

G. Kim et al., "Impedance characterization of a piezoelectric immunosensor Part II: *Salmonella typhimurium* detection using magnetic enhancement," Biosensors and Bioelectronics, vol. 18, 2003, pp. 91-99.

G. Lettieri et al., "A novel microfluidic concept for bioanalysis using freely moving beads trapped in recirculating flows," Lab Chip, vol. 3, 2003, pp. 34-39.

T. P. Burg et al., "Suspended microchannel resonators for biomolecular detection," Applied Physics Letters, vol. 83, No. 13, Sep. 29, 2003, pp. 2698-2700.

A. Piqué et al., "Laser processing of polymer thin films for chemical sensor applications," Surface and Coatings Technology, vol. 163-164, 2003, pp. 293-299.

E. V. Olsen et al., "Specific and selective biosensor for *Salmonella* and its detection in the environment," Journal of Microbiological Methods, vol. 53, 2003, pp. 273-285.

M. Kanai et al., "PDMS Microfluidic Devices with PTFE Passivated Channels," $7^{th}$ International Conference on Miniaturized Chemical and Biochemical Analysis Systems (Oct. 5-9, 2003), p. 429-432.

L. Puckett et al., "Monitoring blood coagulation with magnetoeleastic sensors," Biosensors and Bioelectronics, vol. 18 (2003), pp. 675-681.

C. A. Savran et al., "Microfabricated mechanical biosensor with inherently differential readout," Applied Physics Letters, vol. 83 (2003), pp. 1659-1661.

B. Chadwick et al., "Selecting the Right Material for Medical Seals," Medical Device & Diagnostic Industry Magazine, http:/www.devicelink.com/grabber.php3?URL=htt;://www.devicelink.com/mddi/archive/...(last visited Aug. 13, 2003).

W. C. Tang, "Micro-Biomechanics," University of California Irvine, Department of Biomedical Engineering/Department of Electrical Engineering & Computer Science, (Sep. 2003).

H. Su et al., "Kinetics of interfacial nucleic acid hybridization studied by acoustic network analysis," Biosensors & Bioelectronics, vol. 10, 1995, p. 329-340.

P. Irwin et al., "Blocking nonspecific adsorption of native food-borne microorganisms by immunomagnetic beads with l-carrageenan," Carbohydrate Research, vol. 339, 2004, pp. 613-621.

I. L. Medintz et al., "General Strategy for Biosensor Design and Construction Employing Multifunctional Surface-Tethered Components," Analytical Chemistry, vol. 76, No. 19, Oct. 1, 2004, pp. 5620-5629.

C. H. Ahn et al., "Disposable Smart Lab on a Chip for Point-of-Care Clinical Diagnostics," Proceedings of the IEEE, vol. 92, No. 1, Jan. 2004, pp. 154-173.

M. Andersson et al., "Quartz crystal microbalance-with dissipation monitoring (QCM-D) for real time measurements of blood coagulation density and immune complement activation on artificial surfaces," Biosensors & Bioelectronics, vol. 21, 2004, pp. 79-86.

D. Carter et al., "Fabrication and Measurement of an IC-Compatible GHZ-Range Piezoelectric Longitudinal Bar Resonator," Solid-State Sensor, Actuator and Microsystems Workshop, Hilton Head Island, South Carolina, Jun. 6-10, 2004, pp. 254-257.

J. H. Lee et al., "Effect of mass and stress on resonant frequency shift of functionalized $Pb(Zr_{0.52}Ti_{0.48})O_3$ thin film microcantilver for the detection of C-reactive protein," Applied Physics Letters, vol. 84, No. 16, Apr. 19, 2004, pp. 3187-3189.

V. I. Furdui et al., "Immunomagnetic T cell capture from blood for PCR analysis using microfluidic systems," Lab Chip, vol. 4, 2004, pp. 614-618.

T. Cha et al., "Immobilization of oriented protein molecules on poly-(ethylene glycol)-coated Si(111)," Proteomics, vol. 4, 2004, pp. 1965-1976.

J. Sobek et al., "Substrate Architecture and Functionality," Microarray Technology, (Sep. 2004), p. 32-44.

V. Linder et al., "Reagent-Loaded Cartridges for Valveless and Automated Fluid Delivery in Microfluidic Devices," Analytical Chemistry, vol. 77, No. 1, Jan. 1, 2005, pp. 64-71.

H. Lee et al., "Silicon Bulk Micromachined High Q Film Bulk Acoustic Resonator Devices with Mo/A1N/Mo Structures," Integrated Ferroelectrics, vol. 69, 2005, pp. 323-332.

Microsensors Links, "Magnetically-Excited Flexural Plate Wave Device," website www.sandia.gov/mstc/technologies/microsensors/flexural.html., downloaded May 2, 2005.

QCM-D Technology, http://www.q-sense.com/main.qcmd_html (last visited May 23, 2005) pp. 1-2.

"Microsensors—Thickness Shear Mode Resonators," http://www.sandia.gov/mstc/technologies/microsensors/thicicnessshearmode.html (last visited May 23, 2005), pp. 1-3.

"Tone Burst Generators in Research," http://www.ndt-ed.org/EducationResources/CommunityCollege/Ultrasonics/Equipment-Trans/toneburst.htm (last visited May 3, 2005), pp. 1-2.

Y. Yu et al., "High Quality Silicon-Based AIN Thin Films for MEMS Application," Integrated Ferroelectrics, vol. 69 (2005), pp. 367-374.

R. C. Anderson et al., "Microfluidic Biochemical Analysis System," International Conference on Solid State Sensors and Actuators, Transducers '97, vol. 1, Chicago, Jun. 16-19, 1997, pp. 477-480.

D. Armani et al., "Re-Configurable Fluid Circuits by PDMS Elastomer Micromachining," Proc. of the IEEE Micro Electro Mechanical Systems, Orlando, FL, Jan. 1999, pp. 222-227.

J. Bearinger et al., "PPS-PEG Block Copolymers Render Hydrophobic Surfaces Protein and Cell Resistant," presented at BIOSURF IV, Sep. 20-21, 2001, Lausanne, CH.

C. Cole et al., "A Novel Force Discrimination Assay Using Magnetic Beads," Nova Research, Inc., Alexandria, VA. (last viewed Mar. 12, 2003).

K. S. Breuer, "Design, Fabrication and Performance of MEMS Actuators for Flow Control," in Flow Control and MEMs, Von Karman Institute Lecture Series, Rhode Saint Genese, Belgium, 2002.

J. D. Brewster, "Filtration capture and immunoelectrochemical detection for rapid assay of *Escherichia coli* 0157:H7," Journal of Immunological Methods, vol. 211, No. 1, Feb. 1, 1998, pp. 1-8.

R. Ekins, "Ambient Analyte Assay," Ch. 3, The Immunoassay Handbook, Ed. D. Wild, Elsevier, Boston, 2005, pp. 46-60.

H. Cao et al., "An improved tapered tubular optical waveguide probe for magnetic focusing immunosensors," Proc. of SPIE, vol. 4074, Applications of Optical Fiber Sensors, Aug. 2000, pp. 135-143.

K. V. Sharp et al., "Liquid Flows in Microchannels," Ch. 6, The MEMS Handbook, CRC Press, New York, 2002, pp. 6-1-6-38.

L. Feller et al., "Control of Protein Adsorption Using Poly(propylene sulfide)-block-poly(ethylene glycol) Adlayers: New Potential Candidate for the Modification of Biosensor Chip Surfaces," Laboratory for Surface Science and Technology, ETH Zurich, Switzerland (2004).

A. G. Gehring et al., "Enzyme-linked immunomagnetic electrochemical detection of *Salmonella typhimurim*," Journal of Immunological Methods, vol. 195, No. 1, Sep. 9, 1996, pp. 15-25.

J. A. Harley et al., "Design of Resonant Beam Transducers: An Axial Force Probe for Atomic Force Microscopy," Proc. ASME Int. Mech. Eng. Congress and Expo, vol. 66, 1998, pp. 247-252.

F. Jiang et al., "Flexible Shear Stress Sensor Skin for Aerodynamics Applications," 13th Annual International Conference on Micro Electro Mechanical Systems (MEMS), Jan. 23-27, 2000, pp. 364-369.

C. Mastrangelo, "Adhesion-Related Failure Mechanisms in Micromechanical Devices," Tribology Letters, vol. 3, No. 3, Sep. 1997, pp. 1-13.

J. Molho et al., "Fluid Transport Mechanisms in Microfluidic Devices," Proc. ASME Micro-Electro-Mechanical-Systems (MEMS), 1998.

B. P. Pandian et al., "Biochemical Binding in Microsphere-Based Assays," Proceedings of MSM Conference, 2002, pp. 92-95.

C. J. Bruckner-Lea, "Renewable Surface Biosensors," presented at International Symposium on Ultramicrochemical Process, Taejon, KR, 2002.

S. Pasche et al., "Effects of ionic strength and surface charge on protein adsorption at PEGylated surface," J. Phys. Chem. B, vol. 109, 2005, pp. 17545-17552.

M. A. Rixman et al., "Nanoscale Intermolecular Interactions Between Human Serum Albumin and Alkanethiol Self-Assembled Monolayers," Langmuir, vol. 19, 2003, pp. 6202-6218.

K. S. Ryu et al., "Precision Patterning of PDMS Thin Films: A New Fabrication Method and Its Applications," International Symposium on Micro Total Analysis System (uTAS), Nara, Japan, 2002.

C. A. Savran et al., "Micromechanical Detection of Proteins Using Aptamer-Based Receptor Molecules," Analytical Chemistry, vol. 76, 2004, pp. 3194-3198.

S. S. Iqbal et al., "A review of molecular recognition technologies for detection of biological threat agents," Biosensors & Bioelectronics, vol. 15, 2000, pp. 549-578.

M. J. O'Brien et al., "SPR biosensors: simultaneously removing thermal and bulk-composition effects," Biosensors & Bioelectronics, vol. 14, 1999, pp. 145-154.

C. P. Quinn et al., "Photo-crosslinked copolymers of 2-hydroxyethyl methacrylate, poly(ethylene glycol) tetra-acrylate and ethylene dimethacrylate for improving biocompatibility of biosensors," Biomaterials, vol. 16, 1995, pp. 389-396.

E. L. Adler, "Electromechanical Coupling to Lamb and Shear-Horizontal Modes in Piezoelectric Plates," IEEE Transactions on Ultrasonics, Ferroelectrics, and Frequency Control, vol. 36, No. 2, Mar. 1989, pp. 223-230.

J. G. Wetmur, "DNA Probes: Applications of the Principles of Nucleic Acid Hybridization," Critical Reviews in Biochemistry and Molecular Biology, vol. 26, 1991, pp. 227-259.

Biosite® Inc. Web Site—Products, overview tab, at "http://www.biosite.com/overview/technology.aspx" (last visited May 25, 2005), pp, 1-3.

Biosite® Inc. Web Site—Platforms, platforms tab, at "http://www.biosite.com/overview/platforms.aspx" (last visited May 25, 2005), p, 1.

Biosite® Inc. Web Site—Triage Qualitative—Parasite Panel, products subtab, at http://www.biosite.com/products/paraTechInfo.aspx (last visited May 25, 2005), pp. 1-2.

Boston MicroSystems—Products, products tab, at "http://www.bostonmicrosytems.com/products.shtml" (last visited May 25, 2005), p. 1.

Boston MicroSystems—Microresonator Arrays, microresonator tab, at "http://www.bostonmicrosytems.com/microresonators.shtml" (last visited May 25, 2005), pp. 1-2.

Boston MicroSystems—Chemical Sensors, Chemical Sensors tab, at "http://www.bostonmicrosytems.com/prodcs.shtml" (last visited May 25, 2005), pp. 1-2.

X. Su, et al., "Design and Application of Piezoelectric Quartz Crystal-based Immunoassay," Analytical Sciences, vol. 16, Feb. 2000, pp. 107-114.

Pepper, Jane, "Detection of proteins and intact microorganisms using microfabricated flexural plate silicon resonator arrays," Sensors and Actuators B, vol. 96, 2003, pp. 565-575.

Dube, C. E. et al. "26.1: A SI-Based FPO Sensor Array System with Polymer Microfluidics Integrated on a PCB" IEEE, 2002, pp. 460-465.

Grate et al., "Acoustic Wave Sensors." Sensors Update, 1996, pp. 37-83.

Bailey et al. "DNA-Encoded Antibody Libraries: A Unified Platform for Multiplexed Cell Sorting and Detection of Genes and Proteins," J.Am.Chem.Soc., 207, vol. 129, pp. 1959-1967.

N. Barié, et al., "Covalent bound sensing layers on surface acoustic wave (SAW) biosensors." Biosensors & Bioelectronics (2001), vol. 16, pp. 979-987.

J. Li, et al., "Piezoelectric immunosensor based on magnetic nanoparticles with simple immobilization procedures." Analytica Chimica Acta (2003), vol. 481, pp. 191-198.

Andrä, J., "Surface Acoustic Wave Biosensor as a Tool to Study the Interaction of Atimicrobial Peptides with Phospholipid and Lipopolysaccharide Model Membranes," American Chemical Society (2008), pp. 9148-9153.

* cited by examiner

FIG. 4
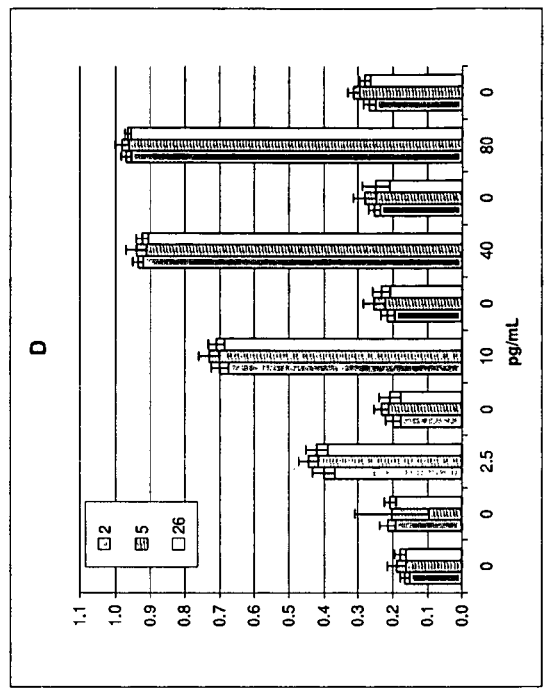
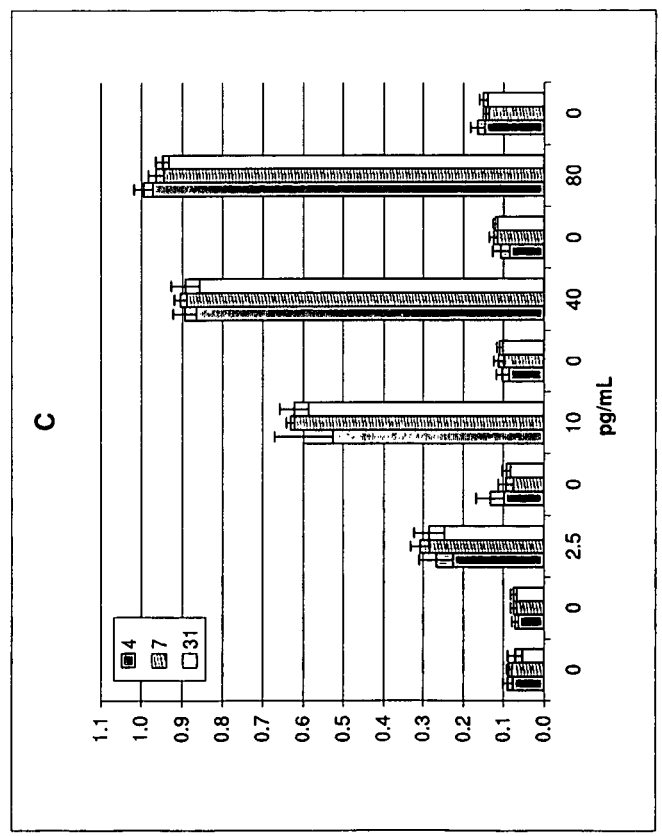

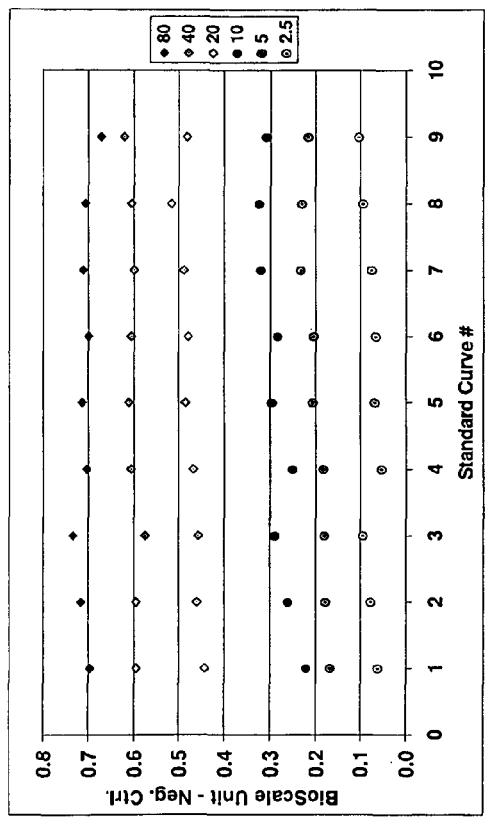
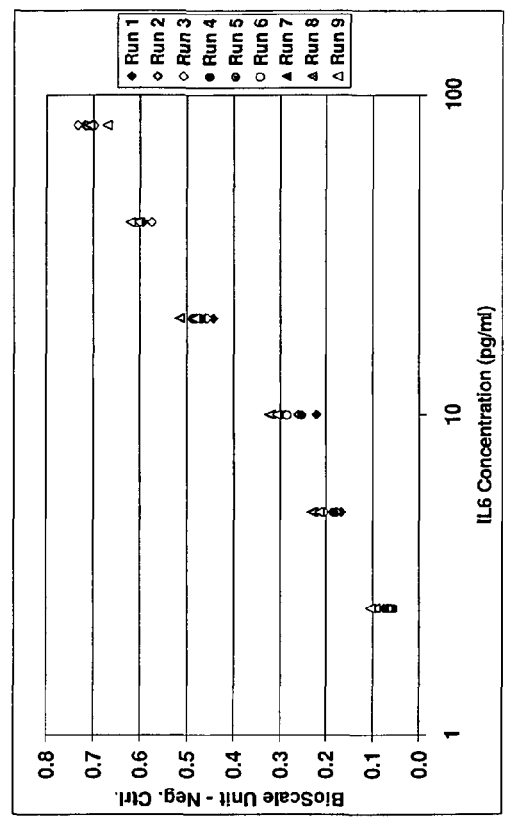
FIG. 7

REUSABLE DETECTION SURFACES AND METHODS OF USING SAME

CROSS-REFERENCE TO RELATED APPLICATIONS

This application claims the benefit of priority to Provisional Application No. 60/970,372, filed on Sep. 6, 2007, and to Provisional Application No. 61/073,243, filed on Jun. 17, 2008. The disclosures of the above applications are incorporated herein by reference in their entirety.

FIELD OF THE TECHNOLOGY

The technology provided herein generally relates to reusable detection surfaces and methods for reusing a detection surface after using the detection surface in an assay for an analyte.

BACKGROUND

Significant challenges exist for a system that detects analytes (e.g., chemical and biological agents) in liquid media include concentration of the analyte in the media, and transport of the analyte to a detection surface, as well as sensitivity, specificity, and reusability. For biological applications, concentration issues generally arise since the concentrations of such analytes tend to be low. Additionally, biological analytes (e.g., cells, cell fragments and macromolecules such as proteins and nucleic acids) tend to be relatively large; hence, transport issues arise because these larger analytes diffuse in fluid solution very slowly.

In addition to cells, cell fragments, and molecules such as proteins and nucleic acids, the detection of small molecule analytes can be a useful marker for diagnosing disease, monitoring drug pharmacokinetics in a patient, and for screening small molecule libraries for potential drug targets. Many therapeutic drugs, including small molecule drugs, require frequent monitoring in patients in order to maximize the beneficial effects of the drug and avoid adverse effects that may result.

Typically, detection of analytes in patient samples requires obtaining the sample in the doctor's office or clinic and sending the sample off site for analysis. Depending on the analyte, the analysis can take one day to several weeks. The results of the analysis are transmitted to the doctor, who then uses the information to adjust treatment as necessary, and contacts the patient to convey the new treatment regimen. The delay associated with analyzing a sample makes it difficult for a doctor to accurately specify a proper treatment.

There is a need for improved assays that can be used to more readily detect analytes, and to detect low concentrations of analyte. In addition, there is a need for improved measurement of analytes including small molecule analytes in order to customize drug regimens to maintain efficacy of the drug while reducing unwanted side effects in individual patients. Furthermore, there is a need for methods and apparatus that can be used at the point of care to measure biologically and/or clinically relevant analytes in order to reduce the delay between obtaining the sample and obtaining the results of the assay.

A key metric for competitive detection is the amount of analyte accumulated on a sensor per unit time. For good performance, the rate of accumulation (and the resulting signal transient) needs to be fast relative to the sensor drift rate. Another key performance metric for an analyte detection system is the degree to which the system can preferentially collect the analyte of interest on the detection surface. Since many biological samples contain extraneous background components (e.g., other proteins, cells, nucleic acids, dirt), it is necessary to prevent these background components from interfering with the desired measurement. So, a transport method that selectively draws the analyte to the sensor and allows interfering background components to pass by has definite advantages. Such a method used in concert with selective binding of the analyte (e.g., antibody, complimentary DNA strands, etc.) to the detection surface can deliver high sensitivity measurements for samples with large amounts of extraneous background components relative to the amount of analyte.

Various methods for improving transport of analyte to a detection surface have been proposed, including filtration, novel flow geometries, acoustic fields, electrical fields (time varying and static) and magnetic fields.

Acoustic excitation has been used to draw cells to field nodes, but it is difficult to use this technique alone to transport material to a surface.

Electrical fields (electrophoresis and dielectrophoresis) have been used to enhance transport but are not universally applicable to all analytes and sample types. They are generally more effective for larger analytes (e.g., cells). Furthermore, the electrical properties of microbes can vary within a given species and strain, making it hard to predict system performance under all intended operating conditions. Sometimes it is necessary to tailor the ionic strength of the sample to improve the performance of the transport. This requirement can conflict with the optimum binding or wash conditions in an assay. Also, electrical fields can dissipate energy and heat conductive fluids (e.g., 0.1 M phosphate buffer solution), which is undesirable since heating can damage the biological analytes.

Immunomagnetic separation (IMS) methods are known in the art for isolating analyte from a sample.

SUMMARY

A sensitive and reusable detection system and methods for reusing a detection surface and systems containing the detection surface are provided. The detection surfaces provided herein can be readily tailored to detect one or more analytes of choice.

Provided herein are cartridges comprising a fluid chamber having at least one detection surface, an antibody or antigen binding fragment thereof (or other suitable capture agent), wherein the suitable capture agent is capable of binding a first non-analyte tag molecule, and wherein the suitable capture agent is linked to the detection surface. The cartridges can be used to detect one or more analytes of interest.

Kits for detecting an analyte of interest are also provided herein. In some embodiments, the kits comprise reagents for detecting the analyte, and a cartridge. In some embodiments, the cartridge comprises a fluid chamber having at least one detection surface comprising an antibody or antigen binding fragment thereof (or other suitable capture agent), wherein the suitable capture agent is capable of binding a first non-analyte tag molecule, and wherein the suitable capture agent is linked to the detection surface.

In some embodiments, the detection surfaces or the cartridges can be reused to detect the same analyte or a different analyte such that the detection surface has similar specificity and sensitivity in subsequent uses as it did in the first use.

Methods of reusing a detection surface are provided. In some embodiments, the detection surface comprises as an antibody or antigen binding fragment thereof (or other suitable capture agent), wherein the suitable capture agent is capable of binding a non-analyte tag molecule, and wherein the suitable capture agent is linked to the detection surface. In some embodiments, the methods of reusing a detection surface comprise, after the detection surface has been used to detect one or more analytes, optionally using a physical method to prepare the detection surface for reuse. In some embodiments, the physical method comprises generating a flow transient over the detection surface.

Physical methods are useful to remove beads (e.g., magnetic particles) from the detection surface, flow chamber, or cartridge containing the detection surface, or combination thereof. Beads on the detection surface due to nonspecific interactions as well as weaker specific interactions and beads remaining in the fluid chamber and/or cartridge can be removed as provided herein. In this way assay reagents (such as magnetic particles) that either non specifically bind to the detection surface and/or those that get caught in regions of poor flow throughout the cartridge between the shut off valve and the pump can be cleared to prepare the detection surface for reuse.

In some embodiments, the detection surface can be prepared for reuse by exposing the detection surface to a wash solution. In some embodiments, a combination of physical methods and exposing the detection to a wash solution can be used. After preparing the detection surface for reuse as provided herein, the detection surface can be used to detect one or more analytes.

In some embodiments, methods of reusing a detection surface comprise instructing or providing instructions to a user to, after the detection surface has been used to detect one or more analytes, generate a flow transient over the detection surface and then to use the detection surface to detect one or more analytes. In some embodiments, methods of reusing a detection surface comprise instructing or providing instructions to a user to, after the detection surface has been used to detect one or more analytes, expose the detection surface to a wash solution, and then to use the detection surface to detect one or more analytes. In still other embodiments, the method of reusing a detection surface comprises instructing or providing instructions to a user to, after the detection surface has been used to detect one or more analytes, generate a flow transient over the detection surface, expose the detection surface to a wash solution, and then to use the detection surface to detect one or more analytes.

Methods for detecting whether one or more analytes is present in a sample are also provided. In some embodiments, the methods for detecting whether one or more analytes is present in a sample comprise introducing a sample and a plurality of magnetic particles coated with a first capture agent capable of binding an analyte into a fluid chamber, wherein at least one surface of the fluid chamber comprises a detection surface and a first antibody or antigen binding fragment thereof (or other suitable capture agent) linked to the detection surface, wherein the first antibody or antigen binding fragment thereof is capable of binding a first non-analyte tag molecule, monitoring a first signal output by the detection surface, generating a flow transient over the detection surface, exposing the detection surface to a wash solution, and repeating the introducing step and monitoring step at least one time.

In some embodiments, methods for detecting whether one or more analytes is present in a sample comprises instructing a user or providing instructions to a user to, after using a detector to detect one or more analytes, optionally generate a flow transient over the surface of the fluid chamber, expose the surface of the fluid chamber to a wash solution and to repeat the step of using the detector to detect one or more analytes at least one time.

In some embodiments, cartridges and kits for detecting one or more analytes in a sample comprise a reusable, analyte specific detection surface. In some embodiments, the cartridges and kits that include the cartridges comprise a detection surface having a capture agent linked thereto, wherein the capture agent is capable of binding an analyte of interest. In some embodiments, the analyte specific detection surfaces or the analyte specific cartridges can be reused to detect the same analyte such that the detection surface has similar specificity and sensitivity in subsequent uses as it did in the first use. In some embodiments, the kit comprises a plurality of magnetic particles coated with a capture agent capable of binding an analyte. In some embodiments, the detection surface bound capture agent has a lower affinity for the analyte than the magnetic particle bound capture agent.

Methods of reusing analyte specific detection surfaces are provided. In some embodiments, the detection surface comprises a capture agent, wherein the capture agent is capable of binding an analyte, and wherein the capture agent is linked to the detection surface. In some embodiments, methods of reusing a detection surface comprise, after the detection surface has been used to detect one or more analytes, using a physical method to prepare the detection surface for reuse. In some embodiments, the physical method comprises generating a flow transient over the detection surface and then optionally using the detection surface to detect one or more analytes. In some embodiments, the methods comprise optionally exposing the detection surface to a chemical wash prior to reusing the detection surface to detect one or more analytes.

In some embodiments, methods of reusing an analyte specific detection surface comprise instructing or providing instructions to a user to, after the detection surface has been used to detect one or more analytes, generate a flow transient over the detection surface, and then to use the detection surface to detect one or more analytes. In some embodiments, the methods comprise instructing the user to optionally expose the detection surface to a chemical wash prior to reusing the detection surface to detect one or more analytes.

Methods for detecting one or more analytes using analyte specific, reusable detection surfaces are also provided. In some embodiments, methods for detecting one or more analytes in a sample comprise introducing a sample and a plurality of magnetic particles coated with a first capture agent capable of binding an analyte into a fluid chamber, wherein at least one surface of the fluid chamber comprises a detection surface and a second capture agent linked to the detection surface, wherein the second capture agent is capable of binding the analyte. In some embodiments, the detection surface monitors the binding of the analyte with a signal output. In some embodiments, the detection surface is cleaned and reused by physical methods, such as by generating a flow transient over the detection surface. In some embodiments, the detection surface is optionally exposed to a wash solution, such as a chemical wash. Further rounds of detection comprise repeating the introducing and monitoring steps at least one time. In some embodiments, the detection surface bound capture agent has a lower affinity for the analyte than the magnetic particle bound capture agent.

In some embodiments, methods for detecting one or more analytes using analyte specific, reusable detection surfaces comprise instructing or providing instructions to a user to after using a detection surface to detect one or more analytes, generate a flow transient over the detection surface, optionally expose the detection surface to a wash solution, and to repeat the step of using the detector to detect one or more analytes at least one time.

The various embodiments described herein can be complimentary and can be combined or used together in a manner understood by the skilled person in view of the teachings contained herein. For example, the detection surface can prepared for reuse by exposing the detection surface to a transient flow and/or to a wash solution in any order after the surface has been used to detect one or more analytes of choice. In addition, the to prepare the detection surface for reuse, the detection surface can be exposed to one or more transient flows or one or more wash solutions in succession, or combinations of one or more transient flows or one or more wash solutions in succession.

BRIEF DESCRIPTION OF THE DRAWINGS

FIG. 7A is a chart of nine repeats of a standard IL-6 concentration curve in serum diluent and B is a graph of the concentration of IL-6 detected in serum mixed with diluent.

DETAILED DESCRIPTION

Figure 1:
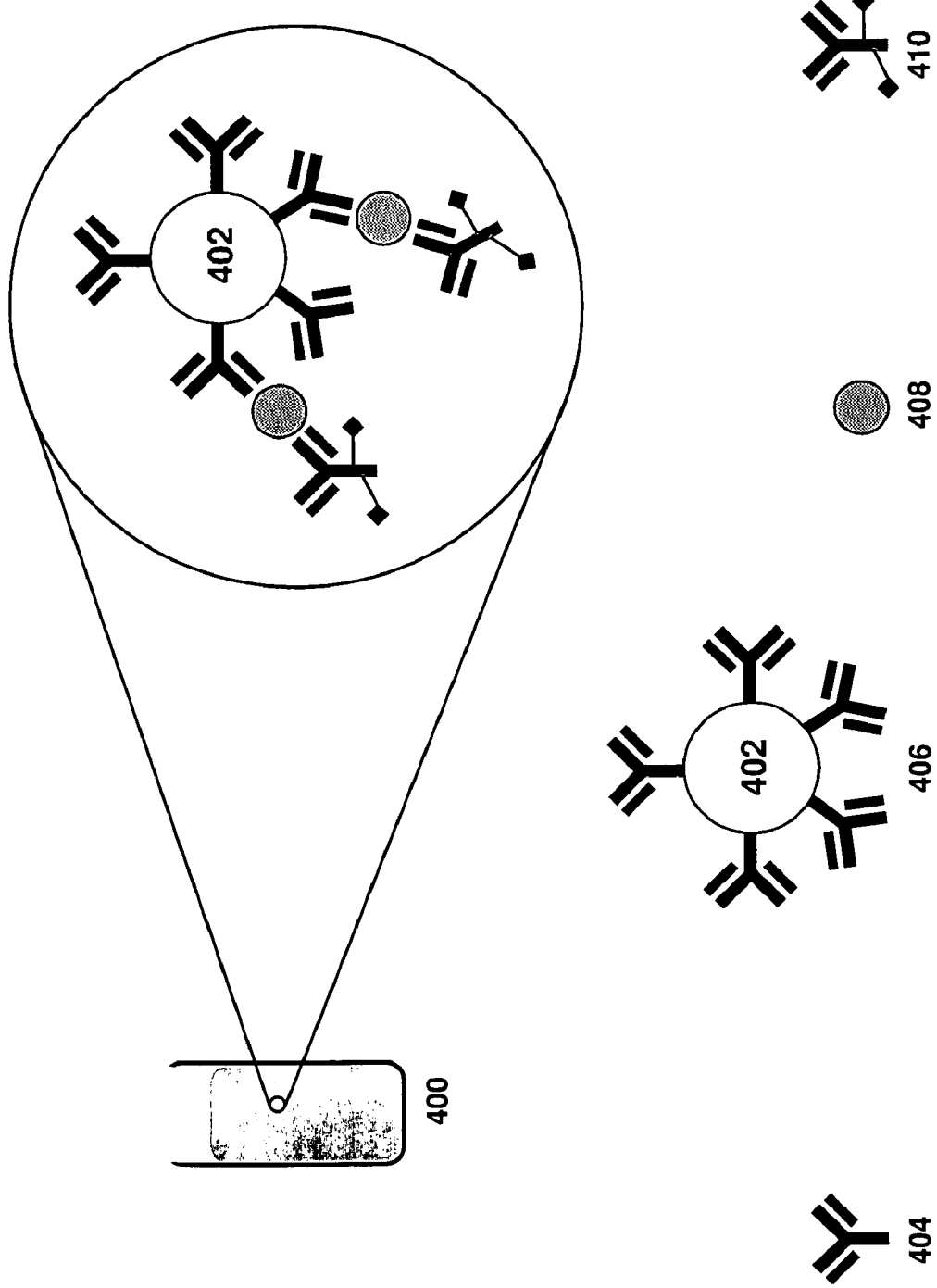
FIG. 1 is a schematic diagram of an embodiment of the technology.

Provided herein are reusable detection surfaces, cartridges comprising the reusable detection surfaces, and methods for using and reusing the detection surfaces to detect one or more analytes. In some embodiments, the detection surface can be readily tailored by the user to detect one or more analytes of choice.

Provided herein are cartridges comprising a fluid chamber having at least one detection surface, a first antibody or antigen binding fragment thereof wherein the first antibody or antigen binding fragment thereof is capable of binding a first non-analyte tag molecule, and wherein the first antibody or antigen binding fragment thereof is linked to the detection surface. The cartridges can be used to detect one or more analytes of interest.

Kits for detecting an analyte are also provided herein. In some embodiments, the kits comprise reagents for detecting the analyte, and a cartridge. In some embodiments, the cartridge comprises a fluid chamber having at least one detection surface comprising a first antibody or antigen binding fragment thereof, wherein the first antibody or antigen binding fragment thereof is capable of binding a first non-analyte tag molecule, and wherein the first antibody or antigen binding fragment thereof is linked to the detection surface.

In some embodiments, the cartridges can be reused to detect the same analyte or a different analyte such that the detection surface has similar specificity and sensitivity in subsequence uses as it did in the first use.

Methods of reusing a detection surface are provided. In some embodiments, the detection surface comprises an antibody or antigen binding fragment thereof, wherein the antibody or antigen binding fragment thereof is capable of binding a non-analyte tag molecule, and wherein the antibody or antigen binding fragment thereof is linked to the detection surface. In some embodiments, the methods of reusing a detection surface comprise, after the detection surface has been used to detect one or more analytes, optionally generating a flow transient over the detection surface; exposing the detection surface to a wash solution, such as a chemical wash, suitable to disrupt the interaction between the capture agent on the detection surface and the non-analyte tag molecule; and using the detection surface to detect one or more analytes.

In some embodiments, methods of reusing a detection surface comprise instructing or providing instructions to a user to, after the detection surface has been used to detect one or more analytes, optionally generate a flow transient over the detection surface, expose the detection surface to a wash solution, and then to use the detection surface to detect one or more analytes.

Methods for detecting whether one or more analytes is present in a sample are also provided. In some embodiments, the methods for detecting whether one or more analytes is present in a sample comprise introducing a sample and a plurality of magnetic particles coated with a first capture agent capable of binding an analyte into a fluid chamber, wherein at least one surface of the fluid chamber comprises a detection surface and a first antibody or antigen binding fragment thereof linked to the detection surface, wherein the first antibody or antigen binding fragment thereof is capable of binding a first non-analyte tag molecule, monitoring a first signal output by the detection surface, generating a flow transient over the detection surface, exposing the detection surface to a wash solution, and repeating the introducing step and monitoring step at least one time.

In some embodiments, methods for detecting whether one or more analytes is present in a sample comprises instructing a user or providing instructions to a user to, use a detector to detect one or more analytes, optionally generate a flow transient over the surface of the fluid chamber, expose the surface of the fluid chamber to a wash solution and to repeat the step of using the detector to detect one or more analytes at least one time.

Provided herein also are cartridges comprising a fluid chamber having at least one detection surface comprising a first capture agent, wherein the first capture agent is capable of binding an analyte, and wherein the first capture agent is linked to the detection surface. The cartridges are analyte specific and can be used to detect one or more analytes of interest.

Kits for detecting an analyte are also provided herein. In some embodiments, the kits comprise reagents for detecting the analyte, and an analyte specific cartridge. In some embodiments, the analyte specific cartridge comprises a fluid chamber having at least one detection surface comprising a first capture agent, wherein the first capture agent is capable of binding an analyte, and wherein the first capture agent is linked to the detection surface.

In some embodiments, cartridges and kits for detecting one or more analytes in a sample comprise an analyte specific detection surface with a capture agent linked to the detection surface, wherein the capture agent is capable of binding an analyte of interest.

In some embodiments, the analyte specific detection surfaces or the analyte specific cartridges can be reused to detect the same analyte such that the detection surface has similar specificity and sensitivity in subsequent uses as it did in the first use.

Methods of reusing an analyte specific detection surface are provided. In some embodiments, the detection surface comprises a capture agent, wherein the capture agent is capable of binding an analyte, and wherein the capture agent is linked to the detection surface. In some embodiments, the methods of reusing a detection surface comprise, after the detection surface has been used to detect one or more analytes, generating a flow transient over the detection surface; optionally exposing the detection surface to a chemical wash suitable to disrupt the interaction between the capture agent on the detection surface and the analyte; and using the detection surface to detect one or more analytes. Suitable chemical washes are described herein.

In some embodiments, methods of reusing an analyte specific detection surface comprise instructing or providing instructions to a user to, after the detection surface has been used to detect one or more analytes, generate a flow transient over the detection surface, optionally expose the detection surface to a wash solution, and then to use the detection surface to detect one or more analytes.

Methods for detecting one or more analytes using analyte specific, reusable detection surfaces are also provided. In some embodiments, methods for detecting one or more analytes in a sample comprise, introducing a sample and a plurality of magnetic particles coated with a first capture agent capable of binding an analyte into a fluid chamber, wherein at least one surface of the fluid chamber comprises a detection surface and a second capture agent linked to the detection surface, wherein the second capture agent is capable of binding the analyte. In some embodiments, the detection surface monitors the binding of the analyte with a signal output. In some embodiments, the detection surface is cleaned and reused, by generating a flow transient over the detection surface, and optionally exposing the detection surface to a wash solution. Further rounds of detection comprise repeating the introducing and monitoring steps at least one time.

In some embodiments, methods for detecting one or more analytes using analyte specific, reusable detection surfaces comprise instructing or providing instructions to a user to, use a detector to detect one or more analytes, generate a flow transient over the detection surface, optionally expose the detection surface to a wash solution, and to repeat the step of using the detector to detect one or more analytes at least one time.

FIG. 1 is a schematic showing an embodiment of the method provided herein wherein a third capture agent 410 is capable of binding the analyte and is coupled to a non-analyte tag molecule (little squares) and the particle 402 has been functionalized with a second capture agent 404 that is capable of binding the analyte 408, the particles having the second capture agent bound thereto 406 and antigen in sample, and analyte 408 are in solution 400. The mixture forms complexes in solution upon incubation for a predetermined period of time according to assay protocol.

Figure 2:
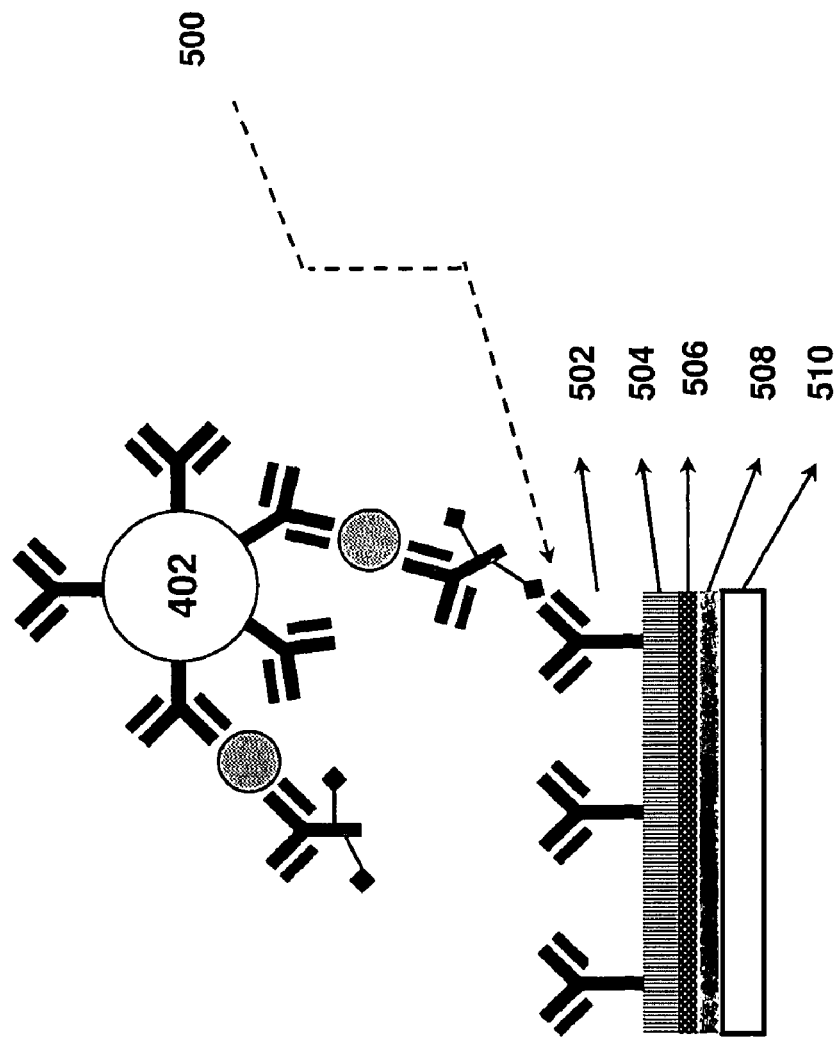
FIG. 2 is a schematic diagram of an embodiment of the technology.

FIG. 2 is a schematic showing the complexes binding detection surface comprising a chip 510 (in some embodiments comprising a gold coated sensor chip) that has been functionalized with a first capture agent 502 that is capable of binding the non-analyte tag molecule. Reference numeral 500 points to a binding site between a non-analyte tag molecule and the first capture agent 502. In one embodiment, the first capture agent is covalently linked to a carboxymethyl dextran (CMD) layer 504, which is in turn linked to a N-(6-aminohexyl)-aminopropyl-trimethoxysilane layer 506, which is in turn linked to a 11-mercapto-1-undecanol layer 508. The binding complexes interact with the detection surface which generates a detectable signal that is proportional (directly or indirectly) to the concentration of analyte in the sample.

Figure 3:
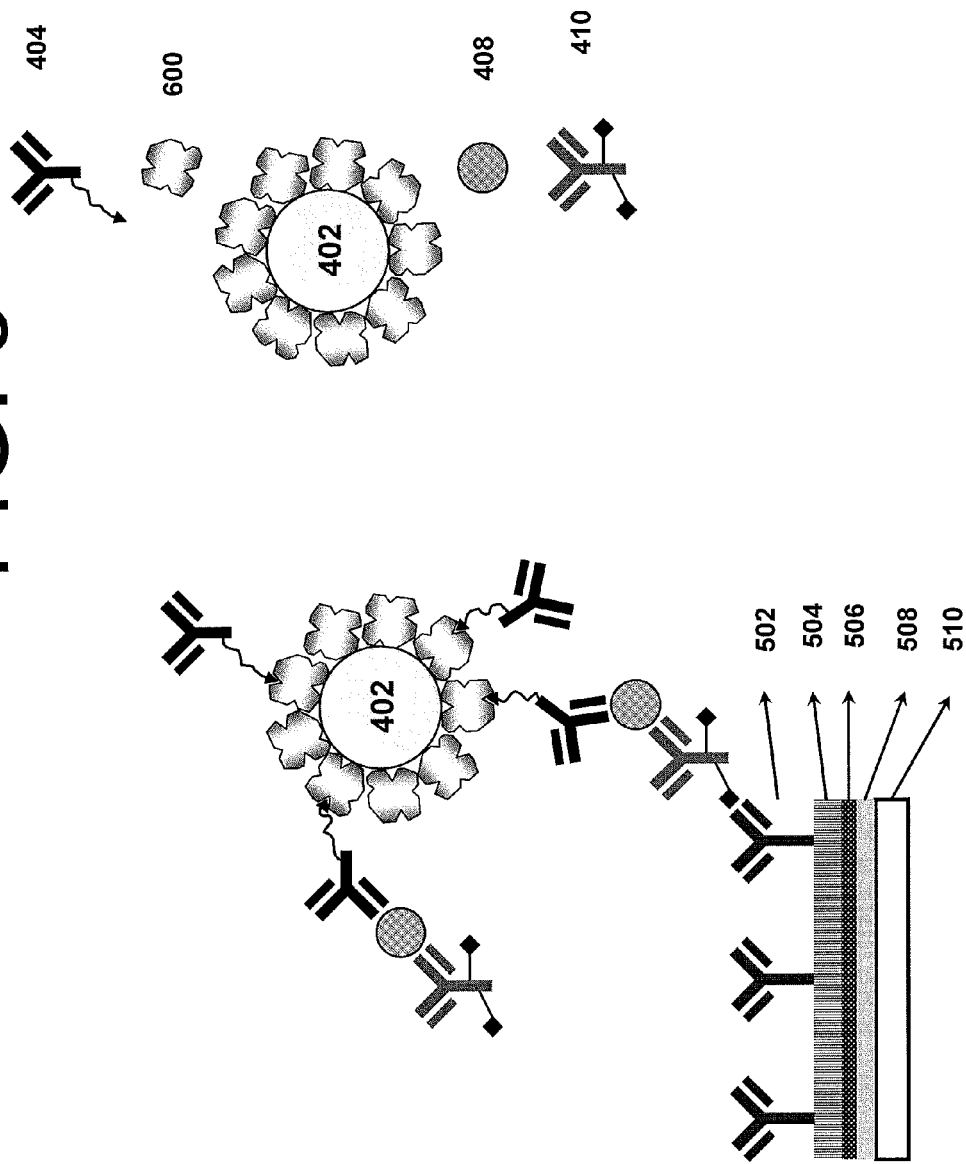
FIG. 3 is a schematic diagram of an embodiment of the technology.

FIG. 3 is a schematic showing another embodiment of the detection surface and methods of using. In this embodiment, the particles 402 are coated with a first member of a binding pair 600 (such as streptavidin), and the second capture agent 404 capable of binding the analyte is linked to the other member of the binding pair 600 (such as biotin). This format allows for use of one particle type to target a variety of analytes.

Figure 9:
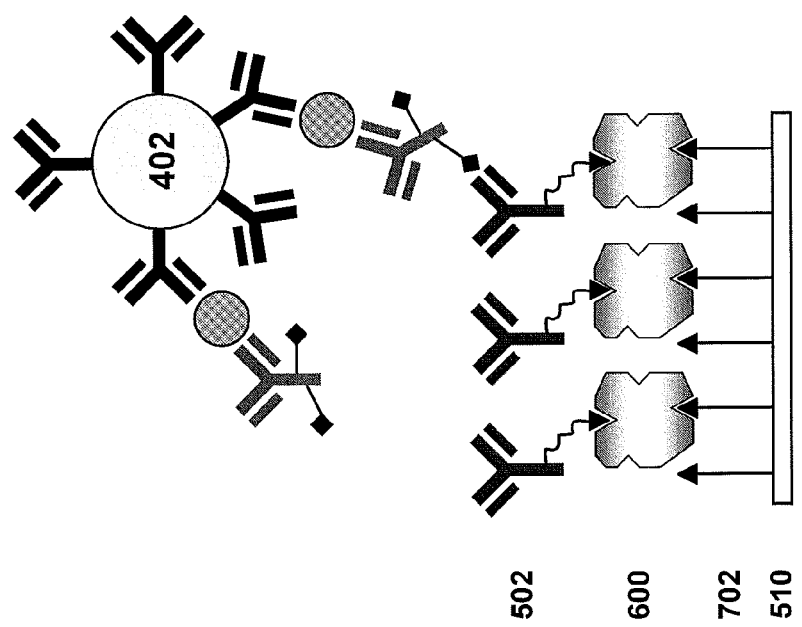
FIG. 9 is a schematic showing another embodiment of the technology.

FIG. 9 is a schematic showing another embodiment where the detection surface comprises a sensor chip 510 is coated with a Biotin-PEG-disulfide Layer 702 which is coupled to one member of a binding pair 600 (such as NEUTRAVIDIN®) to which a first capture agent 502 capable of binding a non-analyte tag molecule is coupled.

Cartridges and kits are provided that comprise a detection surface (or sensor) that can be reused one or more times. In addition, methods of reusing the cartridges and methods of detecting one or more analytes using the reusable detector surfaces described herein are provided.

Detection Surface

Generic Format

Provided herein is a reusable detector surface that can be used to specifically detect a user specified analyte. The reusable detection surface provided herein is pre-coated with a capture agent that is capable of binding a non-analyte tag molecule. The detector surface is regenerable in that after being used in a detection assay, analyte and analyte complexes can be removed from the detection surface while the detection surface retains at least some of the capture agent capable of binding the non-analyte tag molecule such that the specificity and sensitivity of the detection surface is maintained. In some embodiments, the detection surface is pre-coated with a capture agent comprising an antibody or antigen binding fragment thereof. The detection surface can be used to detect any analyte of interest for which there is a capture agent capable of binding the analyte and to which a non-analyte tag molecule can be linked while preserving the capture agents' ability to bind the analyte.

In some embodiments, to specifically detect a user specified analyte, the user can supply or be provided with a capture agent that is capable of binding the analyte of interest. The capture agent capable of binding the analyte of interest is linked to the non-analyte tag molecule such that the analyte-specific capture agent is capable of binding the analyte.

The non-analyte tag molecule can be any compound for which there is a binding partner that can bind to the tag and that can be coupled to the detection surface. Preferably, the tag molecule binds to its binding partner in a substantially specific manner. Tag molecule/binding partner pairs with dissociation constants (KD) of less than about $10^{-6}$ M are preferred. A suitable tag molecule/binding partner pair can be chosen such that there is little, if any, cross-reactivity between the binding partner and the analyte of choice. The tag molecule can be, for example, a small molecule, a hapten, a polypeptide, nucleic acid, aptamer, carbohydrate, nucleoprotein, glycoprotein, glycolipid or lipoprotein. Antibodies or antigen binding fragments thereof are highly suitable as binding partners with the cognate antigen being the non-analyte tag molecule. For example a suitable tag molecule is a hapten, and the binding partner an antibody or antigen binding fragment thereof that is capable of binding the hapten. Suitable haptens are well known in the art and include any small molecule to which a specific antibody can be generated. Suitable haptens include, for example, fluorescein, rhodamine, digoxigenin (DIG), and 2,4-dinitrophenol (DNP) systems and their various derivatives such as tetramethylrhodamine, sulforhodamine, and digoxin. A receptor and its cognate ligand are another example of a possible binding partner/tag molecule pair.

By using the detection surface having a capture agent capable of binding a non-analyte tag molecule bound thereto in combination with a second capture agent that is linked to the non-analyte tag molecule, the same detection surface and/or assay format can be used to detect any analyte for which there is a compatible capture agent. The system is referred to herein as a "generic" format in that a user can use the system with a capture agent that is capable of recognizing an analyte of choice. In some embodiments, the user is provided with components and/or coupling protocols by which the system can be used to detect one or more analytes of choice. The covalent attachment surface chemistry provided herein can be reused multiple times while maintaining specificity and/or sensitivity.

In some embodiments, the detection surface is coated with a material and the capture agent is linked to the material. Suitable materials for attaching the capture agent to the detection surface include, for example, a self-assembling matrix, a CMD layer and the like.

Analyte Specific Format

In some embodiments, the detection surface comprises a capture agent linked thereto, wherein the capture agent is capable of binding to an analyte of interest.

Generic Format Particles

In another embodiment of a generic format, the particles having capture agent bound thereto can be also generic format. In some embodiments, for example as shown in FIG. 3, a capture agent capable of binding the analyte is indirectly linked to the particle. The capture agent can be indirectly linked to the particle using a binding pair as described herein. For example, the particles can be coated with one member of the binding pair, such as streptavidin, and then the user can supply or be provided with a capture agent that is linked to the other member of the binding pair (such as biotin) and that is capable of binding the analyte. In this manner, the particles coated with a member of a binding pair can be used to detect any antigen for which there is a suitable capture agent that can be linked to the other member of the binding pair while retaining the capture agent's ability to bind the analyte.

Flow Transient

In some embodiments, the methods of reusing the detection surface involve flowing the sample over a detection surface. The method also involves, after the detection surface has been exposed to a sample suspected of containing an analyte of interest or a control sample, exposing the detection surface to a flow transient. As described herein, the detection surface can be coated with a material such as a self-assembling matrix or a CMD layer, for example. In some embodiments, the detection surface comprises a capture agent linked thereto, wherein the capture agent is capable of binding to an analyte of interest. In some embodiments, the detection surface comprises a capture agent linked thereto, wherein the capture agent is capable of binding a non-analyte tag molecule.

In some embodiments, a flow transient is generated by restricting the flow of the solution upstream of the detection surface for a first period of time. As used herein, the term solution includes any suitable fluid that can be used to flow over the detection surfaces provided herein. Examples of suitable fluids are described supra, including aqueous fluids, non-aqueous fluids, buffered fluids, and non-buffered fluids. The solutions can include salts, detergents, chelators and the like, as provided supra. The flow of solution can be restricted upstream of the detection surface, for example, by closing or partially closing a valve in the line upstream of the detection surface. In some embodiments, generating the flow transient involves continuing to pump the solution downstream of the detection surface with a fluid pumping source. The pumping source can be, for example, a peristaltic pump or a syringe pump. In some embodiments, generating the flow transient also involves generating a flow transient in combination with a fluctuation in pressure. In some embodiments, generating the flow transient also involves increasing the flow rate of the solution for a second period of time. Any suitable solution can be flowed over the detection surface during the process of generating the flow transient. A suitable solution is one that allows the removal of at least some particles while leaving at least some of the detection surface capture agent bound to the detection surface. In some embodiments, the solution used to run the assay is used during the flow transient process.

In addition, a flow transient can be used to access remote areas of the detection surface that are exposed to sample yet not completely washed and/or cleared by traditional washing. Flow transients can be used in combination with one or more wash solutions to access the remote areas of the detection surface or the flow channel before or after the detection surface that may be present as a consequence of resonant/acoustic device embodiments.

In certain embodiments, the flow transient in combination with a fluctuation in pressure is achieved by gradually releasing the restriction (e.g., opening a valve) while continuing to pump the solution downstream of the detection surface. In some embodiments, a flow transient is used to remove particles from the surface of the sensor because less fluid is required in certain embodiments than could be required if an increase in flow rate alone is used. In one embodiment, the flow transient occurs over a time period between about 0.05 seconds and about 1.0 seconds. In some embodiments, the flow transient in combination with a fluctuation in pressure is achieved by completely and abruptly removing the restriction while pumping. In one embodiment, the flow transient is used in combination with a fluctuation in pressure in preparing a sensor for reuse in which a high concentration of analyte is present in the sample.

In some embodiments, generation of a flow transient results in a pressure drop detected in the pumping mechanism of about −0.5 to −3.0 psi. In some embodiments, the pressure drop is about −1.5 psi.

While not wishing to be bound by theory, the continued pumping with the upstream valve closed lowers the pressure in the line and chamber, including at the detection surface. In some embodiments, a pressure drop of several psi can be achieved. When the valve is released, while the pump is still operating, a flow transient is created. The flow transient in combination with the release of the pressure fluctuation can facilitate clearing the detection surface of at least some of the particles that may have remained post assay procedure. In one embodiment, the flow transient occurs over a time period between about 0.05 seconds and about 1.0 seconds. In certain embodiments, a flow of between about 500 μL/min and about 1000 μL/min for about 10 seconds, washes substantially all the particles away from the detection surface. In some embodiments, a flow of between about 250 μL/min and about 1000 μL/min is used to wash the particles away from the detection surface.

The methods for reusing the detection surface can comprise one or more of the above-described steps for generating a flow transient. This process can be optionally repeated until sensor signals return substantially to signals measured under baseline conditions (e.g., within 50-100 parts per million of the operating frequency measured under a baseline testing condition). In some embodiments, flow alone (for example, a period of 10 seconds of 1000 µL/min flow) strips the detection surface of particles.

In addition, one or more of the above-described steps for generating a flow transient can be repeated. One of ordinary skill in the art, based on the teachings provided herein, will be able to adjust the steps for generating the flow transient to prepare the detection surface for reuse with no more than routine optimization. After subjecting the detection surface to the flow transient, followed by optional washing with a suitable solution, the detection surface is ready for use to analyze a another sample. In this way, detection surfaces (or sensors) can then be reused.

In other embodiments, the interaction between non-analyte tag molecule and the capture agent that is capable of binding the tag molecule can be disrupted. Disruption of the interaction can include a weakening or breaking of one or more non-covalent bonds between the non-analyte tag molecule and the capture agent. Disruption of the interaction can also include breaking a covalent bond between the non-analyte tag molecule and the capture agent. By disrupting the interaction between the non-analyte tag molecule and the capture agent that is capable of binding the tag molecule, the detection surface can be prepared for reuse. Any suitable means for disrupting the interaction between the non-analyte tag molecule and the capture agent that is capable of binding the tag molecule can be used. For example, chemical means can be used. Chemical means can be used to further remove any remaining capture agent that is linked to the non-analyte tag molecule and/or any remaining non-analyte tag molecules. Without wishing to be bound by theory, a suitable wash solution can be chosen to disrupt the interaction between the capture agent capable of binding the non-analyte tag molecule and the non-analyte tag molecule, while allowing the capture agent capable of binding to the non-analyte tag molecule to remain operably inked to the detection surface.

Suitable wash solutions include chemical washes (either buffered or not). Chemical washes can be selected from the general categories of acid, base, detergent, organic solvent, salt solutions, chaotropic agents, and chelating agents. For example, fluids that include formic acid, hydrochloric acid, phosphoric acid, sodium hydroxide, ethylene glycol, sodium chloride, magnesium chloride, guanidine chloride or glycine solutions can be used. Mixtures of different categories of chemical agents as well as mixtures of agents from the same category can also be used.

In some embodiments, the capture agent or antibody or antigen-binding fragment thereof that is linked to the detection surface can have lower affinity for its cognate binding pair than the affinity that the capture agent on the magnetic particle has for its cognate binding pair. The difference in between the capture agent on the detection surface and the capture agent on the particle can be used to facilitate removal of magnetic particles from the detection surface. In this way, significant biologic carry over from one assay to the next using the reusable detection surfaces can be reduced. In some embodiments, higher affinity capture agents are present on the particles, and a lower affinity capture agent is present on the detection surfaces. In some embodiments a suitable ratio of the affinity of the capture agents on the particles relative to the affinity of the capture agents on the detection surfaces is greater than about 2. In some embodiments, the ratio is about 10. Without wishing to be bound by theory, by using a higher affinity capture agent on the particles, the analyte can form a stronger interaction with the particles relative to the interaction between the analyte and the detection surface which comprises a capture agent having a lower affinity. During the process of physically removing the particles, by flowing wash solution, generating a flow transient and combinations thereof, the analyte-capture agent interaction can be disrupted at the weaker detection surface-analyte interaction, thus allowing the removal of the analyte and/or analyte/particle complexes. Thus, in some embodiments of the technology provided herein, the affinity ($K_A$) of the capture agent on the particles is greater than $2 \times 10^9$ $M^{-1}$. In some embodiments, the affinity of the capture agent on the particles is greater than about 2 times the affinity, or equivalent average quantity, of the capture agent on the detection surface.

The flow transient, wash solution, capture agents with different affinities for their targets, generic format detection surface, and generic format particles can be used separately, or can be used in any and all possible combinations.

Detection surfaces can be reused as described herein at least 12-24 times.

Samples

Samples suitable for use in the cartridges, kits, or methods provided herein include any material suspected of containing the analyte. The sample can be used directly as obtained from the source or following one or more steps to modify the sample. In one embodiment, the sample is a biological sample. The biological sample can be derived from any biological source, such as physiological fluids (e.g., blood, saliva, sputum, plasma, serum, ocular lens fluid, cerebrospinal fluid, sweat, urine, milk, ascites fluid, synovial fluid, peritoneal fluid, amniotic fluid, and the like) and fecal matter. The sample can be obtained from biological swabs such as nasal or rectal swabs. In addition, the sample can be biopsy material. The sample can be tissue or tissue lysates, secretions. The sample can be obtained from a human, primate, animal, avian or other suitable source. The sample may also be derived from in vitro systems such from tissue culture or micro organism cultures, for example.

As described herein, the sample can be pretreated prior to use, such as preparing plasma from blood, diluting viscous fluids, and the like. The sample can also be filtered, distilled, extracted, digested with enzyme or concentrated. In one embodiment, a blood sample is obtained from an individual and centrifuged and the plasma is analyzed. The sample can also be treated to inactivate or modify certain activities in the sample capable of interfering with the analyte or the detection process. For example, a decomplexing antagonist can be added to the sample to disassociate the analyte from other molecules that may be bound to and/or may interfere with the ability of the capture agent to bind to the analyte. Such antagonists can be, for example, steroid antagonists. In the case of estradiol detection, the sample can be treated by adding danazol to disassociate estradiol from sex hormone binding protein.

Other samples besides physiological fluids and solids can be used, such as water, food products, and the like, for the performance of environmental or food production assays. For example, the sample can be meat, or poultry wash (the solution used to wash poultry). In addition, a solid material suspected of containing the analyte can be used as the test sample. A solid test sample can be modified (e.g., homogenized, extracted, stomached, or solubilized) to form a liquid medium or to release the analyte.

The sample volume can be as little as 10 µl or as much as 250 ml. In another embodiment, the sample volume is about 1 to about 5 ml.

Capture Agents

Suitable capture agents for use in the present invention include any molecule capable of binding to an analyte of interest. The term "capture agent" includes molecules or multi-molecular complexes that can bind to an analyte of interest. Capture agents preferably bind to their binding partners in a substantially specific manner. Capture agents with equilibrium constants ($K_D$) of less than about $10^{-6}$ M are preferred. The capture agent can also be, for example, polypeptides, proteins, nucleic acids, aptamers, carbohydrates, nucleoproteins, glycoproteins, glycolipids and lipoproteins. Antibodies or antigen binding fragments thereof are highly suitable as capture agents. Antigens may also serve as capture agents, since they are capable of binding antibodies or antigen binding fragments thereof. A receptor which binds a ligand is another example of a possible capture agent. Protein-capture agents are understood not to be limited to agents which only interact with their binding partners through non-covalent interactions. Capture agents may also optionally become covalently attached to the proteins which they bind. For example, the capture agent may be photocrosslinked to its binding partner following binding.

The term "antibody or antigen binding fragment thereof" includes any immunoglobulin, whether naturally produced or synthetically produced in whole, or in part. Derivatives of antibodies that maintain the ability of the antibody to bind to the analyte of interest are also included in the term. The term also includes any protein having a binding domain which is homologous or largely homologous to an immunoglobulin binding domain. These proteins may be derived from natural sources, produced synthetically in whole or in part. An antibody may be monoclonal or polyclonal. The antibody may be a member of any immunoglobulin class, including IgG, IgM, IgA, IgD, and IgE. Where the analyte is known to bind a carrier protein, the antibody can be specific for the free form of the analyte or the carrier-bound form of the analyte. Antibodies that are capable of binding an analyte of choice can be obtained commercially or produced using known methods for generating antibodies.

Antibody or antigen binding fragment thereof refers to any derivative of an antibody which is less than a full-length antibody. Preferably, the antibody fragment retains at least the ability to bind the analyte of interest. Examples of antibody fragments include, but are not limited to, Fab, Fab', F(ab')$_2$, scFv, Fv, dsFv diabody, and Fd fragments. The antibody fragment may be produced by any suitable means. For instance, the antibody fragment may be enzymatically or chemically produced by fragmentation of an intact antibody or it may be recombinantly produced from a gene encoding the partial antibody sequence. Alternatively, the antibody fragment may be synthetically produced in whole or in part. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 50 amino acids and more typically will comprise at least about 200 amino acids.

Single-chain Fvs (scFvs) are recombinant antibody fragments consisting of only the variable light chain ($V_L$) and variable heavy chain ($V_H$) covalently connected to one another by a polypeptide linker. Either $V_L$ or $V_H$ may be the NH$_2$-terminal domain. The polypeptide linker may be of variable length and composition so long as the two variable domains are bridged without serious steric interference. Typically, the linkers are comprised primarily of stretches of glycine and serine residues with some glutamic acid or lysine residues interspersed for solubility. "Diabodies" are dimeric scFvs. The components of diabodies typically have shorter peptide linkers than most scFvs and they show a preference for associating as dimers. An "Fv" fragment is an antibody fragment which consists of one $V_H$ and one $V_L$ domain held together by noncovalent interactions. The term "dsFv" is used herein to refer to an Fv with an engineered intermolecular disulfide bond to stabilize the $V_H$-$V_L$ pair. A "F(ab')$_2$" fragment is an antibody fragment essentially equivalent to that obtained from immunoglobulins (typically IgG) by digestion with an enzyme pepsin at pH 4.0-4.5. The fragment may be recombinantly produced. A "Fab'" fragment is an antibody fragment essentially equivalent to that obtained by reduction of the disulfide bridge or bridges joining the two heavy chain pieces in the F(ab')$_2$ fragment. The Fab' fragment may be recombinantly produced. A "Fab" fragment is an antibody fragment essentially equivalent to that obtained by digestion of immunoglobulins (typically IgG) with the enzyme papain. The Fab fragment may be recombinantly produced. The heavy chain segment of the Fab fragment is the Fd piece.

Suitable polypeptide capture agents also include virtually any peptide, polypeptide, or protein that is capable of binding an analyte of interest, or a small molecule such as a small organic molecule. Suitable polypeptide capture agents may be obtained, for example, commercially, using recombinant methods, using synthetic production methods, or by purification from a natural source. Polypeptides include, for example, cell surface proteins, cell surface and soluble receptor proteins (such as lymphocyte cell surface receptors, steroid receptors), nuclear proteins, signal transduction molecules, transcription factors, allosteric enzyme inhibitors, clotting factors, enzymes (e.g., proteases and thymidylate synthetase, serine/threonine kinases, threonine kinases, phosphatases, bacterial enzymes, fungal enzymes and viral enzymes), proteins associated with DNA and/or RNA synthesis or degradation and the like. As described in more detail below, where more than one capture agent is used, the capture agents can be, for example, isoforms of each other.

In a particular embodiment, where the analyte is a virus, the capture agent can be a cell surface receptor for the virus. For example, where the virus is HIV, the capture agent can be Dendritic cell-specific ICAM-3 grabbing nonintegrin (DC-SIGN) or CD4. In another embodiment the capture agent can be antibodies that are capable of binding viral antigens. For example, the antigen can be gp41 or gp120. The capture agent can be antibodies capable of binding host-derived antigens. For example, the antigen can be CD44, CD54, human leukocyte antigen (HLA) such as HLA-DR, or HLA-DRDPDQ.

The capture agent can also be a nucleic acid such as RNA or DNA, or peptide nucleic acid. In one embodiment, the nucleic acid or peptide nucleic acid is capable of hybridizing to nucleic acid or peptide nucleic acid analyte. In addition, the capture agent can be an aptamer, a nucleic acid capable of binding to non-nucleotide analyte (e.g., proteins, small organic molecules, or inorganic molecules). As used herein, an aptamer can be either an RNA or a DNA chain composed of naturally occurring or modified nucleotides.

Suitable capture agents also include members of binding pairs. Suitable binding pairs include, for example, biotin and avidin or biotin and derivatives of avidin or avidin-like variants (e.g., streptavidin, captavidin, and NEUTRAVIDIN®).

Capture agents such as an antibody or antigen binding fragments thereof that is capable of binding the analyte can be bound to the particle as described below or by using standard techniques for attaching polypeptides, nucleic acids, and the like to surfaces.

Analytes

As used herein, the term "analyte" refers to, an entity whose presence is to be tested in a sample and contains a portion that can be specifically recognized by a capture agent. For example, the term analyte can refer to the epitope recognized by an antibody, or can include that part of a ligand that is bound by a receptor. The term analyte also includes larger molecules that contain a molecular structure that is recognized by a capture agent. The analyte can be part of a cell, for example a cell surface protein. The analyte can be an analyte of interest, chosen by the user (e.g., preselected). The analyte can be selected based on the ability to bind a capture agent of interest, for example in small molecule library screening.

As described herein, the present invention can be used to measure one or more analytes of a panel of analytes. The panel of analytes can include one or more analytes that are detected using a competition format as described herein. The panel of analytes can include one or more analytes detected using the sandwich assay format as described herein. In one embodiment, each analyte is detected using a separate cartridge as described below In order to test a panel of one or more analytes, a single sample can be divided into two or more aliquots. Each aliquot can be tested for a different analyte, for example, using a different cartridge for each analyte to be tested. In this manner, panels of different analytes may be tested without requiring that multiple samples be acquired and/or that different types of apparatus be employed to test the different analytes.

In one embodiment, the analyte of interest is a small molecule. Small molecules include organic or inorganic molecules having a molecular weight of about 1000 g/mol or less. Typically, small molecule analyte will contain a single or only a few binding sites. Competitive binding can be used to detect and/or quantify a small molecule analyte.

The small molecule can include, for example, steroids, lipids, carbohydrates, peptides, and heterocyclic compounds (e.g. bases, including co-factors such as FAD and NADH). The analyte (e.g., small molecule) can be part of a library of small organic molecules which comprise aldehydes, ketones, oximes, hydrazones, semicarbazones, carbazides, primary amines, secondary amines, tertiary amines, N- substituted hydrazines, hydrazides, alcohols, ethers, thiols, thioethers, thioesters, disulfides, carboxylic acids, esters, amides, ureas, carbamates, carbonates, ketals, thioketals, acetals, thioacetals, aryl halides, aryl sulfonates, alkyl halides, alkyl sulfonates, aromatic compounds, heterocyclic compounds, anilines, alkenes, alkynes, diols, amino alcohols, oxazolidines, oxazolines, thiazolidines, thiazolines, enamines, sulfonamides, epoxides, aziridines, isocyanates, sulfonyl chlorides, diazo compounds and/or acid chlorides, preferably aldehydes, ketones, primary amines, secondary amines, alcohols, thioesters, disulfides, carboxylic acids, acetals, anilines, diols, amino alcohols and/or epoxides, most preferably aldehydes, ketones, primary amines, secondary amines and/or disulfides and combinations thereof.

The analyte of interest can also be a polypeptide, a nucleic acid, a carbohydrate, a nucleoprotein, a glycopeptide or a glycolipid. Useful analytes include, for example, enzymes, steroids, hormones, transcription factors, growth factors, immunoglobulins, steroid receptors, nuclear proteins, signal transduction components, allosteric enzyme regulators, and the like. Analytes of interest can be obtained, for example, commercially, recombinantly, synthetically, or by purification from a natural source. In preferred embodiments, the analyte of interest is associated with a specific human disease or condition.

Suitable growth factors include, for cytokines such as erythropoietin/EPO, granulocyte colony stimulating receptor, granulocyte macrophage colony stimulating receptor, thrombopoietin (TPO), IL-2, IL-3, IL-4, IL-5, IL-6, IL-8, IL-10, IL-11, IL-12, TNFα, growth hormone, prolactin, human placental lactogen (LPL), CNTF, and octostatin. Suitable steroids include, but are not limited to, estradiol, progesterone, testosterone, and derivatives thereof. Other suitable analytes include, for example, insulin, insulin-like growth factor 1 (IGF-1), epidermal growth factor (EGF), vascular endothelial growth factor (VEGF), placental growth factor (PLGF),TGF-α and TGF-β), other hormones and receptors such as bone morphogenic factors, follicle stimulating hormone (FSH), and leutinizing hormone (LH), tissue necrosis factor (TNF), apoptosis factor-1 and -2 (AP-1 and AP-2), and mdm2.

In one embodiment, the analyte is a cardiac marker. Cardiac markers are well known in the art and include, for example, c-troponins I and T, myoglobin, creatin kinase MB (CK-MB), and ischemia modified albumin. In one embodiment, the present invention can be used to detect a panel of analytes in order to assess a patient's condition. In one embodiment, a panel of cardiac markers is tested. The panel can include, for example, c-troponin-I, CK-MB, and myoglobin analytes.

In another embodiment, the analyte is a marker for vial infection. Markers for viral infection include, for example, inflammatory markers, circulating viral proteins, CD4+ cells, liver enzymes, and anti-virus antibodies.

The analyte of interest can also be a therapeutic drug where it would be useful to measure the levels of the drug in a patient sample, for example for drug management purposes or patient compliance. Suitable therapeutic drugs include, but are not limited to protease inhibitors and immunosupressants. Suitable protease inhibitors include ageneraser, reyataz, lexiva, telzir, crixivan, kaletra, viracep, norvi, invirase, aortovase, aptivus and the like. Suitable immunosuppressants include cyclosporin, tacrolimus (FK-506), rapamycin, mycophenolic mofetil and the like.

The analyte of interest can be a pathogen or microbe, such as bacteria or bacterial spores, viruses, parasites, prions or other pathogens or their cell wall or surface components such as gram-positive peptidoglycans, lipoteichoic and teichoicacids, and gram-negative endotoxin (e.g., lipopolysaccharide). Bacterial analytes include, for example, *Shigella* sp. such as *Shigella dysenteriae*, *Campylobacter* sp. such as *Campylobacter jejuni*, *Enterococcus* sp. such as *Enterococcus faecalis*, *Bacillus* sp. such as *Bacillus anthracis*, *Yersinia* sp. such as *Yersinia pestis*, *Bordetella* sp. such as *Bordetella pertussis*, *Streptococcal* species, *Staphylococcus* sp. such as *Staphylococcus aureus*, *Mycobacterium* sp. such as *Mycobacterium tuberculosis*, *Clostridium* sp. such as *Clostridium difficile*, *Clostridium tetani*, or *Clostridium botulinum*, *Escherichia* sp. such as *Escherichia coli*, *Salmonella* sp. such as *Salmonella thyphimurim* or *Salmonella enterica*, *Chlamydia* species, *Treponema* sp. such as *Treponema pallidum*, *Neisseria* sp. such as *Neisseria gonorrhoeae*, *Borrelia* sp. such as *Borrelia burgdorferi*, *Vibrio* sp. such as *Vibrio cholerae*, *Corynebacterium* sp. such as *Corynebacterium diphtheriae*, and *Helicobacter* sp. such as *Helicobacer pylori*. Parasites include, for example, Giardia, malaria and crytosporidia. Viral analytes include, for example, Rhinovirus, Yellow Fever, Group B Coxsachieviruses, (CB1, CB2, CB3, CB4, CB5, and CB6), Canine Parvovirus (CPV), Herpes Simplex virus type 1 (HSV1), Vaccina Virus, T4-like virus, Adenovirus, Influenza B virus, Influenza A, Avian flu, rhinovirus, coronavirus (e.g., SARS), Human Immunodeficiency virus (HIV), Hepatitis viruses, Herpes virus, West Nile Virus, and Ebola virus.

Assay Formats

In some embodiments of the cartridges, kits, and methods provided herein, a plurality of magnetic particles is introduced into a fluid chamber. The magnetic particles are coated with a capture agent capable of binding the analyte and at least one surface of the fluid chamber comprises a sensing surface that has been coated with an antibody or antigen binding fragment thereof that is capable of binding a non-analyte tag molecule. The detection surface can be coated with the antibody or antigen-binding fragment thereof that is capable of binding a non-analyte tag molecule using any suitable method. For example, the surface can be coated with biotin as described herein and then the biotinylated surface can be exposed to the antibody or antigen-binding fragment thereof that is linked to a molecule that binds biotin such as avidin or a derivative of avidin. In another embodiment, the antibody or antigen binding fragment thereof that is capable of binding a non-analyte tag molecule is covalently linked to the detection surface or to a coating on the detection surface. The antibody or antigen-binding fragment thereof is linked to the detection surface such that at least some of the antigen binding portion(s) of the antibody or antigen-binding fragment thereof are capable of binding the cognate antigen.

In the methods provided herein, the particles can be exposed to the sample using a variety of different orders of exposure. For example, in one embodiment, the particles are exposed to the sample and then introduced into the fluid chamber. The sample may be concentrated prior to introducing the sample-exposed particles into the fluid chamber. The sample may be concentrated by, for example, removing the particles from the solution and resuspending the particles in a smaller volume of liquid.

In another embodiment, the sample is introduced into the fluid chamber prior to introducing the particles. In still another embodiment, the particles are introduced into the fluid chamber prior to adding the sample to the fluid chamber.

Control Signal/Normalization

In another embodiment, the signal output of the acoustic device in response to sample exposure is compared to or normalized with a control signal. The control signal can be provided to or obtained by the user. For example, the control signal can be a value provided to the user based on the specific analyte, capture agent, or particular model, version or type of device being used. In one embodiment, the control signal is obtained on a lot basis. For example, the control signal can be a signal that is representative of a particular lot of analyte acquired by the user. The representative signal can be, for example, experimentally derived before, during or after testing of a sample. In some embodiments, the control signal is a standard curve that is obtained by, for example, analyzing known quantities of analyte with a specific capture agent and specific version of the detection surface.

In another embodiment, the control signal is obtained on a use basis. For example, a unique control signal can be obtained each time a particular analyte and/or capture agent is tested on a particular detection surface. In one embodiment, the control signal is obtained using the same analyte and/or capture agent, however, in the absence of sample. The control signal can be obtained before or after running the sample over the detection surface. The detection surface can be prepared for reuse as described herein, and then the sample or control can be run over the same detection surface.

In some embodiments, detection surfaces are cleaned and reused using one or more wash solutions and optionally one or more flow transients. In one experiment, a detection surface comprising eight sensors were cleaned of magnetic beads by adapting and modifying the flows and flow transient procedures described in U.S. application Ser. No. 11/502,168, and was reused up to 20 times over a span of two days. Given an 8 sensor chip, a 96 well plate may optionally be addressed, 8 samples at a time, where controls and calibration standards are mixed into the layout of the plate. There are many possibilities. Calibration standards and/or controls may be provided to specific individual sensors and run at the same time. For example, if 0 sensors are used to generate results for known inputs, 8 sensors are available for unknown samples. If 1 sensor is used to generate results for a known input, 7 sensors are available for unknown samples. Alternately serial assay runs of known calibration standards and controls may be run prior to, interlaced in time with, or after unknown samples.

Reuse enables serial and/or sequential controls and/or calibrations to be run on sensors. One use of the invention involves determining a background measurement prior to the introduction of unknown samples. In this embodiment, magnetic beads are mixed in a calibration sample matrix (known not to contain analyte) and run over the sensor before the unknown samples mixed with beads are introduced and run over the sensor surface. The background measurement, and associated sensor statistics across the chip, serve as a threshold for detection, or alternatively, establish the baseline adjustment used for quantification curves. This background measurement also serves as a control for the operation and integrity of the beads' reagent used in the assay process. In some embodiments, beads that exhibit abnormally high background (beads that are prone to stick) in calibrant or control solutions, are not used in the assay. In some embodiments, because either the beads' reagent or the sensor surface's reagent could be causing the high background, a user would be inclined to replace either the beads' reagent or the sensor surface's reagent.

Optionally, positive calibrations (using calibrant fluids that include a known quantity of analyte) can be serially run to provide assay process controls. In some embodiments, the calibrations can be run interlaced in sequence with a plurality of unknown samples or used to set a calibration curve for quantification of subsequent, or prior, unknown samples. Estimates of unknown quantities can be determined from calibration curves fit to the "known" data.

Optionally, known samples (both negatives and positives) can be run as calibration samples prior to a single run of unknown samples. These known sample runs can be made while the unknown sample is incubating. The positives can be used to set the slope of the calibration curve and the negatives can be used to set the detection limit background. A preferential order for the known samples and unknown samples can be conducted (e.g., positive samples followed by a negative sample run, with the negative sample run setting the sensing background levels just prior to introduction of unknown samples).

Reuse of sensors was demonstrated on two types of sensors. The first type of sensor design used is described in U.S. Pat. No. 6,688,158 and U.S. patent application Ser. No. 11/183,484. The second type of sensor design used is described in U.S. patent application Ser. No. 11/604,645.

Detection Surface

In some embodiments, the detection surface comprises an acoustic device. Acoustic devices couple to fluids predominantly through acoustic interaction between the device and the fluid. Typical acoustic devices include surface acoustic wave devices, flexural plate wave devices, lamb wave devices and cantilever devices. Acoustic devices also couple to fluids through some viscous interaction between the device and the fluid; however, the coupling is predominantly acoustic coupling. Viscous interaction devices couple to fluids predominantly through viscous interaction between the devices and the fluid. Typical viscous interaction devices include quartz microbalance (QCM) devices, shear harmonic surface acoustic wave devices, and acoustic plate mode devices. The term "surface acoustic wave" refers to the manner in which energy is carried in the device structure rather than how the device couples to the fluid. Acoustic devices are devices where fluid interacts over a substantial area of a plane of the device. Acoustic devices respond with substantial out of plane motion that couples acoustically to fluid in proximity to the plane of the device (i.e., kinetic energy, potential energy and losses are carried predominantly in the fluid). Viscous interaction devices respond primarily with in-plane motion that does not couple acoustically to fluid in proximity to a plane of the device.

For applications involving, for example, the detection and quantification of biological or chemical substances in a fluid, the coupling between an acoustic device and a fluid is typically between about 100 nm and about 10 microns in thickness relative to the plane of the device where the coupling between a viscous interaction device and a fluid is between about 10 nm and about 100 nm in thickness relative to the plane of the device.

Surface acoustic wave devices and shear harmonic surface acoustic wave devices both carry energy in their respective structures in similar manners. Surface acoustic wave devices acoustically couple significantly to fluids while shear harmonic surface acoustic wave devices couple to fluids predominantly through viscous interaction.

The following U.S. Patents and Patent Applications, all of which are hereby incorporated by reference, describe examples of the various types of FPW devices suitable for use in the present technology: U.S. Pat. Nos. 5,129,262, 5,189,914, 6,688,158 B2, U.S. patent application Ser. No. 10/324,685, U.S. Pat. Nos. 5,668,303, 5,836,203, and U.S. Patent Application 20040038195.

For example, U.S. Pat. No. 5,129,262 describes an ultrasonic sensor that has a thin planar sheet of material forming a Lamb wave propagation medium. Lamb waves, also known as plate-mode waves, can propagate only through a material of finite thickness. In contrast to surface acoustic waves (SAWs), which require a propagation medium having a thickness on the order of hundreds of times the wavelength of the propagating SAW, Lamb waves require a propagation medium which is at most only several wavelengths thick, and typically only a fraction of the wavelength of the propagating Lamb wave. The thickness of the sheet is no greater than about twenty microns. A Lamb wave generator generates Lamb waves in the planar sheet, and an output device produces an electrical signal that represents the propagation characteristics of the Lamb waves propagating along the sheet. A measuring device measures selected characteristics of the output electrical signal. The planar sheet has some physical characteristics that depend upon the value of an analyte acting on the sheet, and those physical characteristics consequently determine the propagation characteristics of the Lamb waves that propagate along the sheet. Since the electrical signal from the output device represents the propagation characteristics, the electrical signal also represents the value of the analyte acting on the sheet.

The Lamb wave device described in U.S. Pat. No. 5,129,262 can be employed, for example, in biological sensing. The planar sheet described above can be pre-coated with antibody molecules, so that the frequency of the device changes upon immersion in or contact with a liquid that contains the corresponding antigen. Antigen-antibody attachment at the surface of the propagation medium acts to alter the wave velocity of the Lamb waves in the sheet. The change in wave velocity causes the oscillation frequency to change in a delay line oscillator form of the device. Also, the sheet may be made of a porous and permeable material, allowing the coating of antibody molecules over a greater surface area of the sheet and also allowing the antigen-containing liquid to be flowed through the membrane, in order to speed up the antigen-antibody attachment. Other biological interactions may also be sensed, and additional applications include immunoassay, clinical laboratory testing, in vivo biomedical monitoring, and biomedical research.

In some embodiments, capture agents targeting the analyte of interest can be immobilized on the thin layer of gold covering the inner surface of the membrane. The surface can be coated with a suitable linking compound. Suitable linking compounds are commercially available. In one embodiment, the linking compound comprises biotin PEG disulfide, as described below. In another embodiment, thiol-terminated alkyl chains are linked to the gold surface forming self-assembled monolayers (SAMs). A fraction of the SAMs is terminated with reactive groups (e.g., carboxyl or alcohol) to allow covalent linking of capture agents to the SAMs using biochemical process steps known in the art. The remainder of the SAMs can be terminated with non-reactive groups (e.g., alkyl chain). Other surface chemistries are described in the literature and can be used to produce a capture surface.

In some embodiments, assays are generally run as described in U.S. application Ser. No. 11/183,484, "Method and Apparatus for Detection of Analyte Using a Flexural Plate Wave Device and Magnetic Particles," (the teachings of which are incorporated herein in their entirety). Sample volumes (e.g., volume between about 10 μL and about 10 mL) are mixed with suspended particles that are specific for the analyte of interest. Particles are typically suspended in a diluent and are added to raw sample in proportion according to a specified method (e.g., 10% through 90% sample dilutions are typically run). The mixture is incubated for a period of time, as per a determined protocol for a given analyte. Incubation allows for the analyte to be captured by the particles in accordance with kinetic binding principles.

The incubated mixture is flowed over the detection surface and particles are attracted to the detection surface by applying magnetic field gradient in close proximity to the detection surface. In certain embodiments, the sensor is a flexural plate wave (FPW) sensor and the output signals of the sensor are monitored. The signals change in proportion to the amount of magnetic particles located at and/or near the detection surface. Using these signals, measurements are made of the net exposure level of particles relative to a baseline measured when no particles are loaded on to the detection surface. The net exposure signal level relative to the baseline signal sets a range, which can be multiplied by any scalar to represent any normal units. An example choice of a scalar is the average number of exposed particles across sensors, using the approximate relation of between about 0.5 and 1.0 parts per million in frequency change per particle. The units would roughly correspond to number of particles on the detection surface.

After exposing the detection surfaces to sample, and washing the particle loaded detection surfaces in a solution with the magnetic field applied, the magnetic field is removed and a wash protocol specific to the assay is conducted. While the wash protocol is conducted, flow speeds can be either incremented discretely, linear stepped, nonlinear stepped or logarithmically stepped.

The FPW signals, normalized by exposure levels, are integrated over the period of time the wash protocol is conducted and are recorded. Calibration curves are generated when the processed signals are correlated with samples having known standard fluids mixed into calibration liquids. Quantities present in unknown samples are determined by comparing the processed sensor signals to the calibration curves. In addition to integration, proportional, integral and rate measurements can be made over a variety of time points during the dissociation period to, for example, provide additional information to a user.

EXAMPLE 1

Preparation of the Detection Surface

Materials: absolute ethanol (200 proof), ethanolamine (99%, Sigma-Aldrich), 1× phosphate buffered saline (PBS), deionized (DI) water, 11-mercapto-1-undecanol (11-MUO, 97%, Sigma-Aldrich, Product#: 447528), N-(6-aminohexyly)aminopropyl trimethoxysilane (AHPTS, 95%, Gelest, Inc., Product#: SIA0954.0), 1-ethyl-3-[3-dimethylaminopropyl]carbodiimide hydrochloride (EDC, Pierce, Product#: 22981), N-hydroxysuccinimde (NHS, Sigma-Aldrich, Product#: 130672), carboxymethyl dextran (CMD, Sigma-Aldrich, Product#: 86524), anti-FITC antibody (Ab, Jackson ImmunoResearch Laboratories, Inc.) (1 mg/mL or 0.5 mg/mL in 1× PBS), and flexural plate wave (FPW) chips.

Functionalization of FPW chips with 11-MUO.

A 5 mM stock solution of 11-MUO in ethanol was prepared making sure that the 11-MUO was completely dissolved in the ethanol. A 1 mM 11-MUO solution was made by diluting the appropriate amount of 5 mM 11-MUO stock solution in ethanol.

Cleaned FPW chips were placed in 800 μL of 1 mM 11-MUO and incubated overnight at room temperature. FPW chips were cleaned, for example, using solvent and $O_2$ plasma.

Functionalization of 11-MUO Chips with N-(6 aminohexyl) aminopropyltrimethoxysilane (AHPTS).

A 1 wt % AHPTS solution in ethanol was prepared and thoroughly mixed.

11-MUO was wicked away from the chips and the 11-MUO chips were transferred to absolute ethanol and incubated for 5 min to remove residual 11-MUO from the detection surfaces.

Ethanol was wicked away from the chips and the chips were incubated in 1% AHPTS overnight at room temperature.

Functionalization of 11-MUO/AHPTS chips with carboxymethyl dextran (CMD)

A CMD solution was prepared by adding 150 mg of CMD to 50 mL of ultrapure water and mixed thoroughly. Nine-hundred sixty mg of EDC was added to the CMD solution prepared and mixed thoroughly. Five-hundred seventy-five mg of NHS was added to the CMD+EDC solution and mixed thoroughly.

The chips were transferred to ethanol and incubated for 5 min to remove residual AHPTS from the detection surface. The chips were transferred to DI water, and incubated for 10 min to remove residual ethanol from the detection surface. The chips were then blotted to remove excess DI water, transferred to CMD+EDC/NHS solution, and incubated for 8 hr allowing the CMD to be immobilized on 11-MUO/AHPTS surface.

Activation of 11-MUO/AHPTS/CMD chip with EDC/NHS.

Nine-hundred sixty mg of EDC was added to ultrapure water and mixed thoroughly. Five-hundred seventy-five mg of NHS was added to the EDC solution and mixed thoroughly (5 min of mixing).

The chips were transferred to DI water, and incubated for 5 min to remove residual CMD+EDC/NHS solution from the detection surface. The chips were blotted to remove DI water, transferred to the EDC/NHS solution, and incubated for 30 min allowing the CMD surfaces to be activated with NHS ester.

Functionalization of 11-MUO/AHPTS/CMD chips with Antibody.

A 50 μg/mL solution of antibody was prepared in 1× PBS and the solution was thoroughly mixed. The chips prepared as described above were incubated in DI water for 5 min to remove residual EDC/NHS from the detection surface.

The chips were then blotted to remove excess water and transferred to the 50 μg/mL solution of antibody and incubated overnight at room temperature. Two chips were incubated together in one eppendorf tube with electrode-side facing each other.

Quenching of CMD/Ab Chips

A 100 mM solution of ethanolamine was prepared in 1× PBS and thoroughly mixed. The Ab chips were then transferred to DI water and incubated for 10 min. The chips were then blotted to remove excess water and incubated in the ethanolamine solution for 30 min to quench the unreacted portion of activated CMD on detection surface.

Stabilization of CMD/Ab Chips

The Ab chips were then transferred to DI water and incubated for 10 min to remove residual ethanolamine from the detection surface. The chips were then blotted to remove excess water and incubated in a stabilizer that maintains the activity of antibodies and other biomolecules adsorbed or immobilized to solid substrates (e.g., 1× STABILGUARD® IMMUNOASSAY STABILIZER (BSA-FREE) SurModics) for 2 hrs at room temperature.

Drying Stabilized Ab Chips

The Ab chips were blotted to remove excess stabilizer and transferred onto chip holders. The Ab chips-loaded chip holders were incubated in dry box overnight.

Cleaning Electrodes of Stabilized Ab Chips for Mounting

The Ab chips were removed from the dry box, placed on water-wet kimwipes with electrode-side facing down, and incubated for 30~60 sec.

The chips were carefully removed from the wet kimwipes and placed on dry kimwipes so no water entered into the wells. The electrode sides of the chips were dried using $N_2$. The chips were then stored in eppendorf tubes in a drybox or mounted onto cartridges and packaged.

EXAMPLE 2

IL-6 Assay on Carboxymethyl Dextran (CMD)-mediated Antibody Chips

The antibody coupled to the surface in this example was the BioLegend (Product#: 501204, Purified anti-human IL-6 antibody, Clone#: MQ2-39C3). Particles used were substantially the same as in previous examples (coupled according to Invitrogen (Dynal) recommended methods for tosyl activated particles, using BD Biosciences capture antibody from Kit Cat. No 555220).

Preparation of sample mixtures. IL-6 was added to 5 ml of buffer (1× PBS with 0.05% Tween™ 20 (Polyoxyethylene- 20-sorbitan Monolaurate)) to generate IL-6 analyte samples with various concentrations. A 1:100 dilution of the anti-IL-6 particle stock (anti-IL-6 IgG coated particles) was prepared in 1× PBS with 0.1% bovine serum albumin (BSA). Diluted particles were added to 5 ml of assay diluent (Becton, Dickinson and Company) such that the final particle concentration was $1 \times 10^5$ particles/ml. The diluent tubes and the sample tubes were incubated end-over-end for at least 5 minutes. Each diluent tube was added to its corresponding sample tube and incubated end-over-end for 200 min at room temperature.

The samples were analyzed using an FPW device where the detection surfaces were functionalized with anti-IL-6 antibody on carboxymethyl dextran layers.

After the detection was completed, the detection surfaces (e.g., anti-IL-6 antibody on carboxymethyl dextran) were cleaned by flowing 25 mM phosphoric acid at 1000 ml/min for 20 seconds followed by flowing assay running buffer (1× PBS with 0.05% Tween™ 20 (Polyoxyethylene-20-sorbitan Monolaurate)) at 1000 ml/min for 2 minutes. A pressure pulse (flow transient) is applied immediately following flowing the assay running buffer, resulting in removing residual samples (e.g., IL-6) from the detection surfaces.

Figure 4:
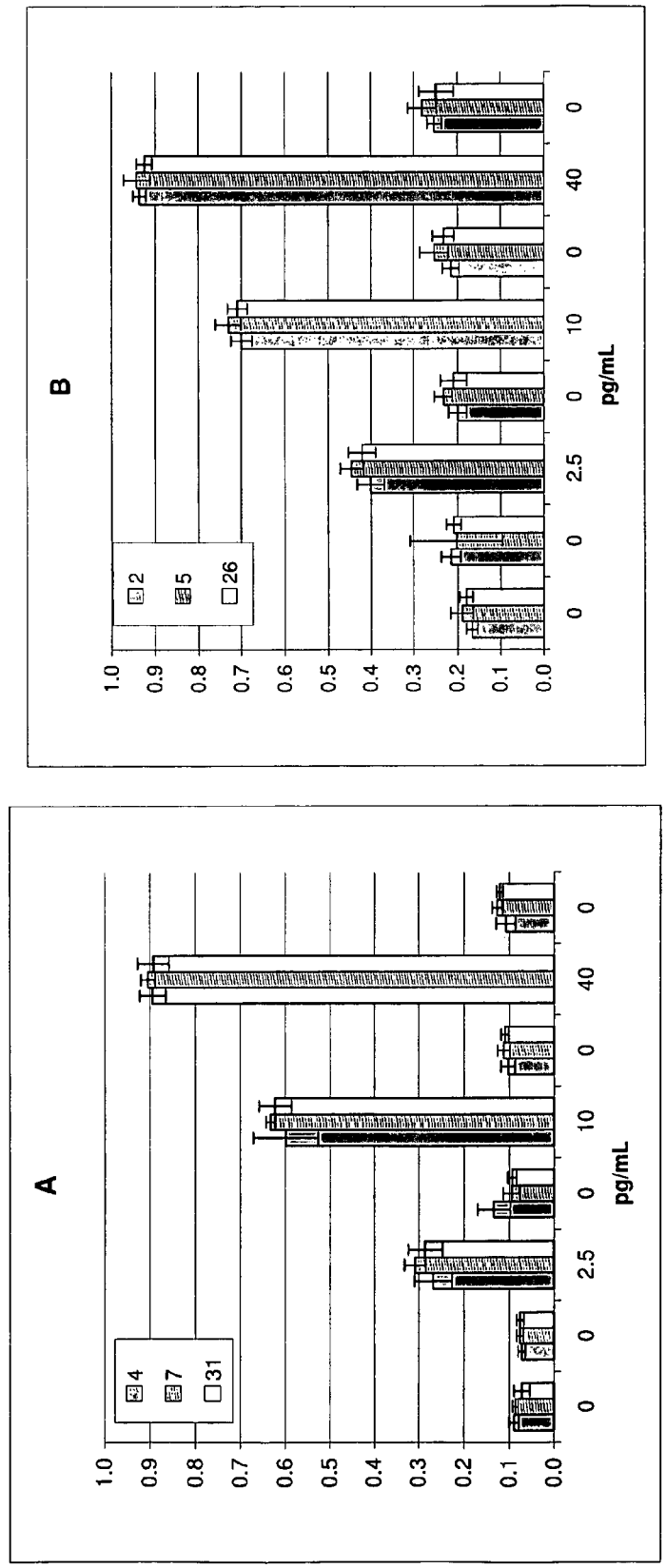
FIG. 4(A-D) are bar graphs showing the detection of IL-6.

Additional rounds of detection of analyte samples were conducted using the cleaned detection surfaces. The detection surfaces are now primed for an additional round of detection of analyte samples. The resulting data are shown in FIG. 4. FIG. 4 shows graphs of standard curve samples interlaced with negative controls demonstrating that the surface is reusable after analyte at the indicated concentrations were spiked into pooled heat treated charcoal stripped serum samples (B and D) or PBST diluent (A and C).

EXAMPLE 3

IL-6 Detection using a Reusable, Generic Format, System

Preparation of sample mixtures. IL-6 was added to 5 ml of buffer (1× PBS with 0.05% Tween™ 20 (Polyoxyethylene-20-sorbitan Monolaurate)) or human serum to generate IL-6 protein analyte samples with various concentrations. A 1:100 dilution of the anti-IL-6 particle stock (anti-IL-6 IgG coated onto tosylactivated 2.8 µm particles at a concentration of ~$10^9$ particles/ml prepared according to manufacturer's instructions) was prepared in 1× PBS with 0.1% BSA. An appropriate amount of the diluted particles was added to 5 ml of assay diluent (Becton, Dickinson and Company) such that the final particle concentration was $1 \times 10^5$ particles/ml. An appropriate amount of fluorescein-labeled anti-IL-6 IgG (BioLegend, labeling reaction performed according to manufacturer's instructions) was added to each of the assay diluent tubes such that the final fluorescein-labeled anti-IL-6 IgG concentration was 0.2 ug/ml or 0.05 ug/ml. The concentration of fluorescein-labeled anti-IL-6 IgG and the degree of labeling can be varied to modulate the sensitivity and dynamic range of the assay of interest. The diluent tubes and the sample tubes were incubated end-over-end for at least 5 minutes. Each diluent tube was added to its corresponding sample tube and incubated end-over-end for 3 hours at room temperature.

The samples were analyzed using an FPW device where the detection surface was covalently functionalized with anti-fluorescein antibody (Jackson ImmunoResearch Laboratories, clone 1F8-1E4) on carboxymethyl dextran layers. As illustrated in FIG. 4, higher concentration of IL-6 present in the sample resulted in a higher level of fluorescein-labeled capture agent binding on the particle surface, which translated into higher signal output from the sensor due to increased binding between fluorescein and surface-immobilized anti-fluorescein antibodies.

After the detection was completed, the detection surface was cleaned with 25 mM phosphoric acid by flowing the acid through the sensor surface at 1000 µl/min for 20 seconds. Assay running buffer (1× PBS with 0.05% Tween™ 20 (Polyoxyethylene-20-sorbitan Monolaurate)) was immediately introduced over the sensor at 1000 µl/min for 2 minutes followed by mechanical pressure pulses in the flow.

Detection followed by 25 mM phosphoric acid wash was repeated 12 times without deterioration of sensor sensitivity or specificity.

Figure 5:
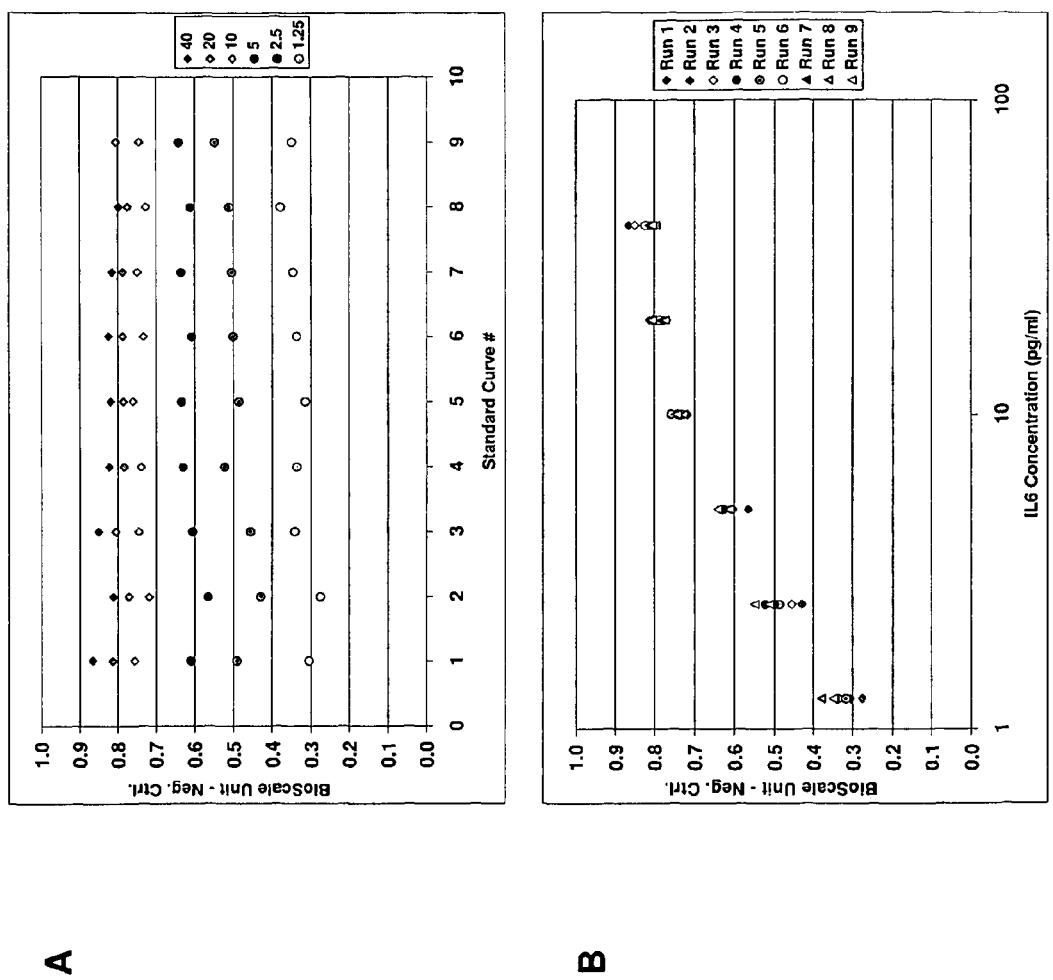
FIG. 5A is a chart of nine repeats of a standard IL-6 concentration curve in PBS diluent and B is a graph of the concentration of IL-6 detected in PBS mixed with diluent.

FIG. 4 (A and C) shows a typical dose-dependent sensor response in an IL-6 assay in PBS Tween™ 20 (Polyoxyethylene-20-sorbitan Monolaurate)) buffer/diluent. Each sample contained fluorescein-labeled secondary capture antibody at a concentration of 0.1 µg/ml. The labeling reaction was done using 10:1 ratio of fluorescein-NHS ester molecules to secondary capture antibody molecules. The FPW sensors were exposed to samples containing the indicated concentration of IL-6 analyte (displayed from left to right on the horizontal axes of FIG. 4). Throughout the experiment, three standard sample runs were performed followed by one run of negative control where all sensors were exposed to samples containing 0 pg/ml of IL-6. Twenty-five mM of phosphoric acid wash (described in the assay procedure) was carried out in between each of the 12 runs to clean the functional surface. FIG. 5 demonstrates the consistency of signals arising from individual analyte concentration (1.25 pg/ml IL-6 to 40 pg/ml IL-6 (FIG. 5B) across the 9 standard curve runs (FIG. 5A). Signal for each IL-6 concentration was calculated by subtracting the negative control signal from the signal of the sample containing IL-6 of specified concentration. FIG. 5B shows the sensor response with respect to the analyte concentration in semi-log format.

Figure 6:
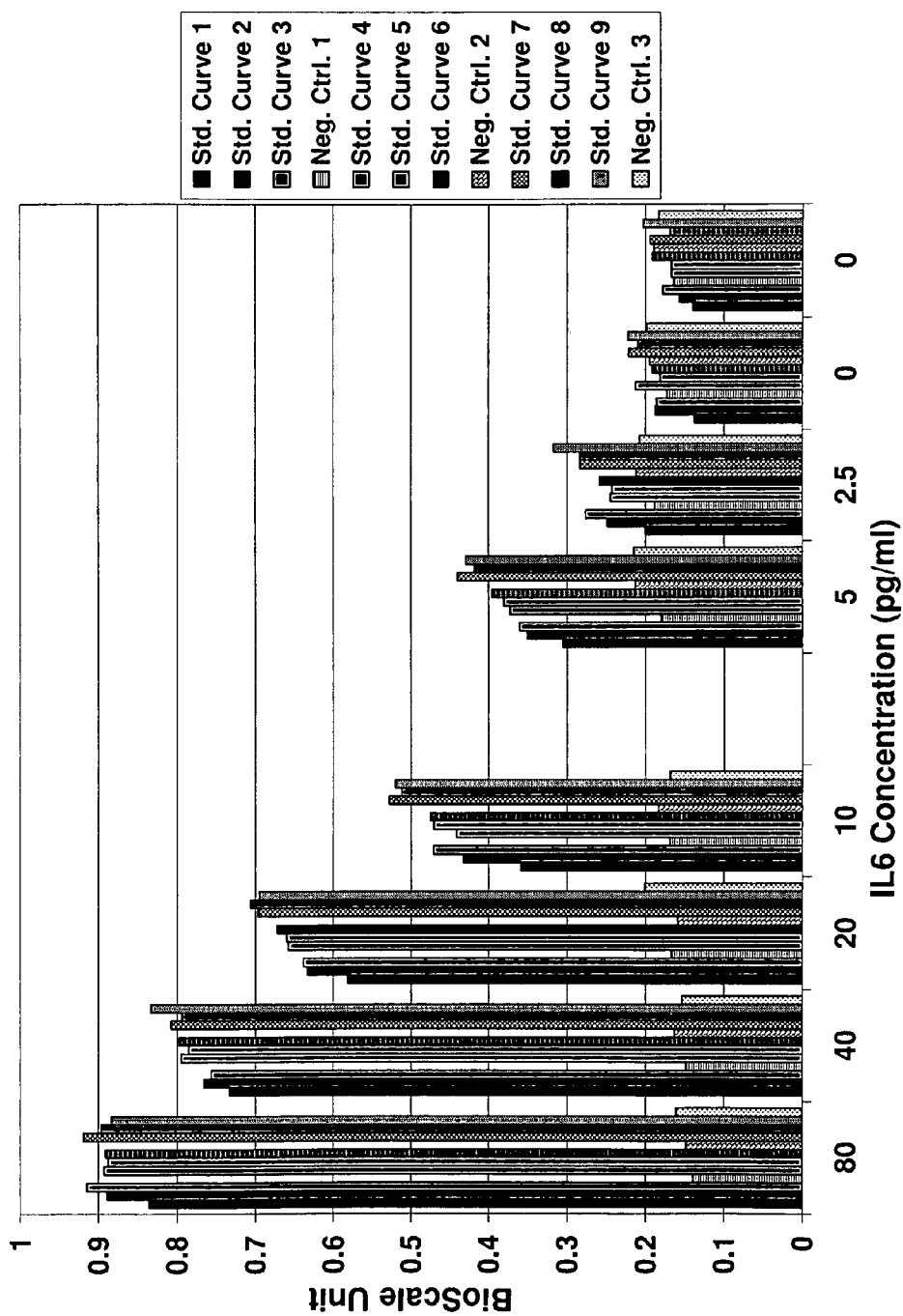
FIG. 6 is bar graph of IL-6 concentration detected in serum mixed with diluent.

FIGS. 6 and 7 show the same types of plots as FIGS. 4 and 5 respectively, except the results shown were an IL-6 assay in serum mixed with diluent. Each sample contains fluorescein-labeled secondary capture antibody at a concentration of 0.025 µg/ml. The labeling reaction was done using 24:1 ratio of fluorescein-NHS ester molecules to secondary capture antibody molecules. The FPW sensors 1, 2, 3, 4, 5, 6, 7, and 8 were exposed to samples containing 80, 40, 20, 10, 5, 2.5, 0, and 0 pg/ml of IL-6 analyte, respectively (displayed from left to right on the horizontal axis of FIG. 6).

EXAMPLE 4

Detection of IL-6 using an Anti-Dig Detection Surface

Figure 8:
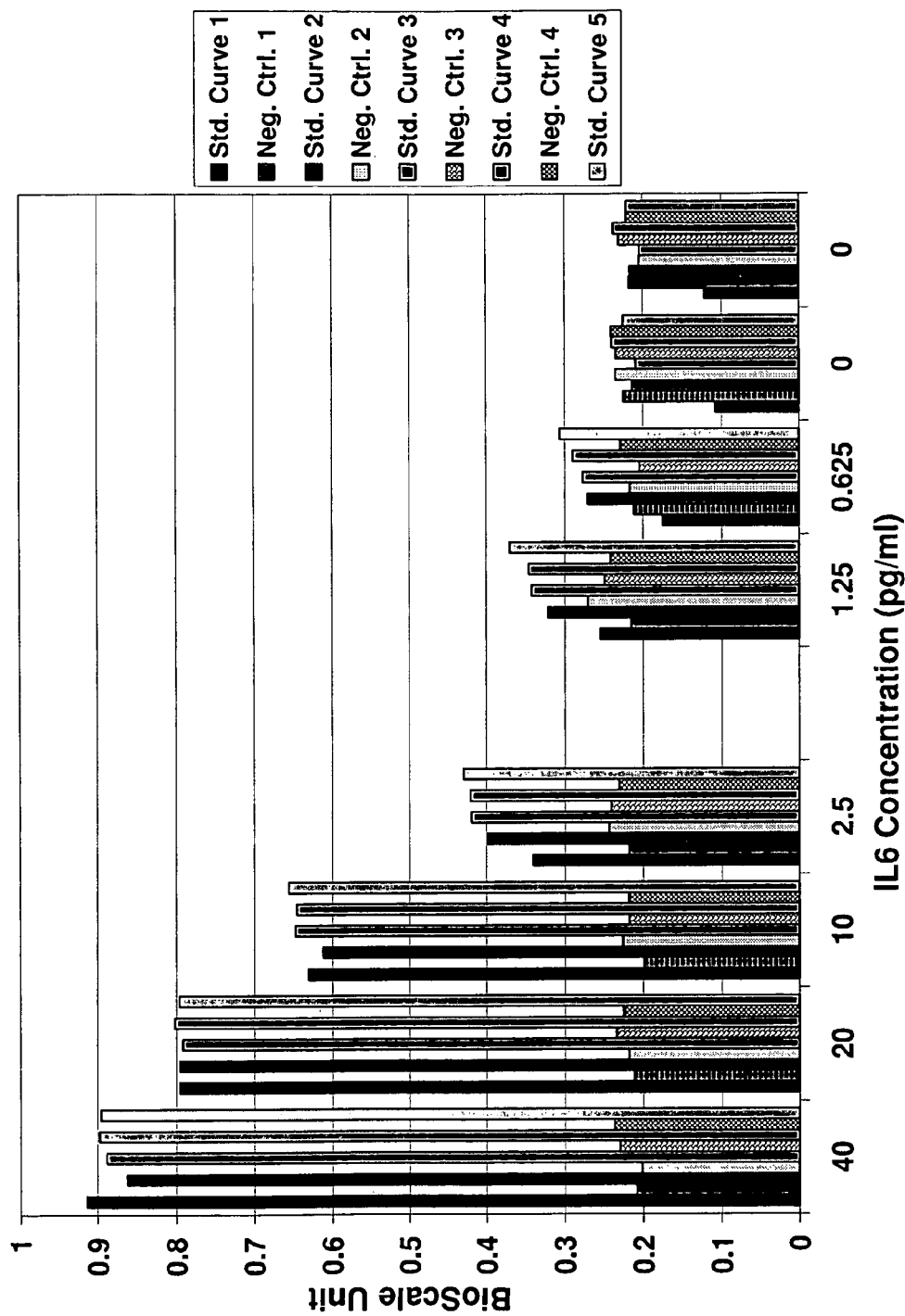
FIG. 8 is a bar graph of IL-6 concentration.

FIG. 8 shows a dose-dependent sensor response for a 9-run IL-6 assay in PBS Tween™ 20 (Polyoxyethylene-20-sorbitan Monolaurate) with diluent matrix using digoxigenin (DIG)-labeled anti-IL-6 antibody and a detection surface coated with anti-DIG IgG coupled to CMD. Each sample contained DIG-labeled anti-IL-6 antibody at concentration of 0.1 µg/ml. The labeling reaction was performed using 10:1 ratio of DIG-NHS (Roche Applied Science) molecules to anti-DIG antibody (Roche Applied Science). The consistency of the signals was evaluated by 5 standard curve runs interlaced with 4 runs of negative controls.

While the technology has been particularly shown and described with reference to specific illustrative embodiments, it should be understood that various changes in form and detail may be made without departing from the spirit and scope of the technology.

We claim:

1. A method comprising:
   introducing a sample including a plurality of magnetic particles and an analyte into a fluid chamber including a detection surface comprising an acoustic device having a vibrating membrane and a first capture agent linked to the detection surface, wherein the sample includes at least one magnetic particle, of the plurality of magnetic particles, functionalized with a second capture agent capable of binding the analyte bound to a third capture agent coupled to at least one non-analyte tag molecule;
   binding the non-analyte tag molecule to the first capture agent and binding the second capture agent to the analyte;
   monitoring, using the detection surface, a first signal output generated by interaction of the vibrating membrane and the plurality of magnetic particles; and
   generating a flow transient over the detection surface for removing the non-analyte tag molecule from the first capture agent;
   removing the non-analyte tag molecule from the first capture agent while the first capture agent remains linked to the detection surface so that the first capture agent is reusable.

2. The method of claim 1 wherein the first capture agent has a lower binding affinity for the non-analyte tag molecule than the second capture agent has for the analyte.

3. The method of claim 1 further comprising:
   binding a second non-analyte tag molecule of the sample to the first capture agent;
   monitoring, using the detection surface, a second signal output generated by interaction of the vibrating membrane and the plurality of magnetic particles; and
   removing the second non-analyte tag molecule from the first capture agent while the first capture agent remains linked to the detection surface.

4. The method of claim 1 further comprising exposing the detection surface to a solution to remove the non-analyte tag molecule from the first capture agent.

5. The method of claim 3 further comprising exposing the detection surface to a solution to remove the non-analyte tag molecule from the first capture agent prior to binding the second non-analyte tag molecule of the sample to the first capture agent.

6. The method of claim 1 further comprising restricting flow of the chemical wash upstream of the detection surface while pumping flow of the chemical wash downstream of the detection surface and then removing the restriction after a first period of time to generate the flow transient.

7. The method of claim 3 further comprising generating a flow transient over the detection surface to remove the non-analyte tag molecule from the first capture agent prior to binding the second non-analyte tag molecule of the sample to the first capture agent.

8. The method of claim 7 further comprising restricting flow of the chemical wash upstream of the detection surface while pumping flow of the chemical wash downstream of the detection surface and then removing the restriction after a first period of time to generate the flow transient.

9. The method of claim 4 wherein the solution comprises one of a salt solution, a phosphate buffered saline, or phosphoric acid.

10. The method of claim 4 wherein the solution is acidic.

11. The method of claim 3 wherein the first signal output is suitable to detect a first concentration of the analyte and the second signal output is suitable to detect a second concentration of the analyte, wherein the second concentration is at least 50% less than the first concentration of the analyte.

12. The method of claim 1 wherein the first capture agent is an antibody or antigen binding fragment thereof.

13. The method of claim 1 wherein the affinity of the second capture agent for the analyte is greater than $2 \times 10^9$ $M^{-1}$.

14. The method of claim 1 wherein the affinity of the second capture agent for the analyte is greater than about 2 times the affinity of the first capture agent for the analyte.

* * * * *